(12) United States Patent
Lawrence et al.

(10) Patent No.: US 11,242,367 B2
(45) Date of Patent: Feb. 8, 2022

(54) SILK-DERIVED PROTEIN FOR TREATING INFLAMMATION

(71) Applicant: Silk Technologies, Ltd., Plymouth, MN (US)

(72) Inventors: Brian D. Lawrence, Tampa, FL (US); David W. Infanger, Maple Grove, MN (US)

(73) Assignee: Silk Technologies, Ltd., Plymouth, MN (US)

(*) Notice: Subject to any disclaimer, the term of this patent is extended or adjusted under 35 U.S.C. 154(b) by 8 days.

(21) Appl. No.: 16/324,844

(22) PCT Filed: Aug. 12, 2017

(86) PCT No.: PCT/US2017/046659
§ 371 (c)(1),
(2) Date: Feb. 11, 2019

(87) PCT Pub. No.: WO2018/031973
PCT Pub. Date: Feb. 15, 2018

(65) Prior Publication Data
US 2019/0169243 A1 Jun. 6, 2019

Related U.S. Application Data

(60) Provisional application No. 62/467,697, filed on Mar. 6, 2017, provisional application No. 62/407,863, filed on Oct. 13, 2016, provisional application No. 62/374,532, filed on Aug. 12, 2016.

(51) Int. Cl.
| | |
|---|---|
| *C07K 14/435* | (2006.01) |
| *A61K 9/00* | (2006.01) |
| *A61K 38/00* | (2006.01) |
| *A61K 47/02* | (2006.01) |
| *A61K 47/18* | (2017.01) |
| *A61K 47/34* | (2017.01) |
| *A61K 47/38* | (2006.01) |
| *A61K 47/26* | (2006.01) |
| *A61K 38/01* | (2006.01) |
| *A61K 47/10* | (2017.01) |
| *A61F 2/14* | (2006.01) |
| *A61K 47/42* | (2017.01) |

(52) U.S. Cl.
CPC .......... *C07K 14/43586* (2013.01); *A61F 2/14* (2013.01); *A61K 9/0048* (2013.01); *A61K 38/012* (2013.01); *A61K 47/02* (2013.01); *A61K 47/10* (2013.01); *A61K 47/183* (2013.01); *A61K 47/26* (2013.01); *A61K 47/34* (2013.01); *A61K 47/38* (2013.01); *A61K 47/42* (2013.01); *A61K 38/00* (2013.01)

(58) Field of Classification Search
CPC ......... A61F 2/14; A61K 38/00; A61K 38/012; A61K 47/02; A61K 47/10; A61K 47/183; A61K 47/26; A61K 47/34; A61K 47/38; A61K 47/42; A61K 9/0048; A61P 27/02; A61P 27/06; A61P 29/00; A61P 43/00; C07K 14/43586
See application file for complete search history.

(56) References Cited

U.S. PATENT DOCUMENTS

| | | | |
|---|---|---|---|
| 5,468,743 A | 11/1995 | Janssens et al. | |
| 5,591,426 A | 1/1997 | Dabrowski et al. | |
| 5,880,283 A | 3/1999 | Matsumoto et al. | |
| 5,895,645 A | 4/1999 | Dabrowski et al. | |
| 6,034,220 A | 3/2000 | Stedronsky | |
| 6,280,747 B1 | 8/2001 | Philippe et al. | |
| 6,333,045 B1 | 12/2001 | Yasueda et al. | |
| 6,562,873 B2 | 5/2003 | Olejnik et al. | |
| 6,627,210 B2 | 9/2003 | Olejnik et al. | |
| 6,641,834 B2 | 11/2003 | Olejnik et al. | |
| 6,673,337 B2 | 1/2004 | Olejnik et al. | |
| 7,030,149 B2 | 4/2006 | Chang et al. | |
| 7,060,260 B2 | 6/2006 | Fahnestock et al. | |
| 7,115,388 B2 | 10/2006 | Tsubouchi | |
| 7,193,038 B2 | 3/2007 | Tsubouchi et al. | |
| 7,314,938 B2 | 1/2008 | Shen et al. | |
| 7,320,976 B2 | 1/2008 | Chang et al. | |
| 7,323,463 B2 | 1/2008 | Chang et al. | |

(Continued)

FOREIGN PATENT DOCUMENTS

| | | |
|---|---|---|
| CN | 101194666 A | 6/2008 |
| CN | 102860969 A | 1/2013 |

(Continued)

OTHER PUBLICATIONS

Ruan et al. ('An investigation into the effect of potassium ions on the folding of silk fibroin studied by generalized two-dimensional NMR-NMR correlation and Raman spectroscopy' FEBS Journal v275 2008 pp. 219-232) (Year: 2008).*
Kim et al., J Neurosurg 114:485-490, 2011 (Year: 2011).*
Lawrence, et al., "Silk Film Biomaterials for Cornea Tissue Engineering," Biomaterials 30(7), 1229-1308 (Mar. 2009).
Applegate et al., "Photocrosslinking of Silk Fibroin Using Riboflavin for Ocular Prostheses," Adv Mater., 28(12):2417-2420, Mar. 2016.

(Continued)

*Primary Examiner* — Larry D Riggs, II
*Assistant Examiner* — Joseph Fischer
(74) *Attorney, Agent, or Firm* — Haukaas Fortius PLLC; Michael H. Haukaas

(57) ABSTRACT

Described herein are methods for reducing inflammation by administration of an effective amount of silk-derived proteins (SDP) or a fraction thereof to a subject having an inflammatory condition. The methods include the treatment of inflammatory conditions and wounds, including corneal wounds, comprising the topical administration of an effective amount of SDP material as described herein.

18 Claims, 9 Drawing Sheets

Specification includes a Sequence Listing.

(56) References Cited

U.S. PATENT DOCUMENTS

| | | |
|---|---|---|
| 7,351,404 B2 | 4/2008 | Woodward et al. |
| 7,388,029 B2 | 6/2008 | DeLong et al. |
| 7,635,755 B2 | 12/2009 | Kaplan et al. |
| 7,642,258 B2 | 1/2010 | Chang et al. |
| 7,745,460 B2 | 6/2010 | Shen et al. |
| 7,790,743 B2 | 9/2010 | Shen et al. |
| 7,842,714 B2 | 11/2010 | Farnes et al. |
| 7,851,504 B2 | 12/2010 | Chang et al. |
| 7,928,122 B2 | 4/2011 | Shen et al. |
| 8,008,338 B2 | 8/2011 | Muller et al. |
| 8,038,988 B2 | 10/2011 | Woodward et al. |
| 8,084,047 B2 | 12/2011 | Shen et al. |
| 8,097,583 B2 | 1/2012 | Scheibel et al. |
| 8,101,161 B2 | 1/2012 | Woodward et al. |
| 8,133,890 B2 | 3/2012 | Chang et al. |
| 8,168,655 B2 | 5/2012 | Gadek et al. |
| 8,207,215 B2 | 6/2012 | Muller et al. |
| 8,263,054 B2 | 9/2012 | Woodward et al. |
| 8,278,353 B2 | 10/2012 | Chang et al. |
| 8,299,118 B2 | 10/2012 | Chang et al. |
| 8,309,605 B2 | 11/2012 | Chang et al. |
| 8,338,479 B2 | 12/2012 | Chang et al. |
| 8,354,409 B2 | 1/2013 | Chang et al. |
| 8,361,617 B2 | 1/2013 | Kaplan et al. |
| 8,367,701 B2 | 2/2013 | Burnier et al. |
| 8,377,982 B2 | 2/2013 | Muller et al. |
| 8,420,077 B2 | 4/2013 | Altman et al. |
| 8,481,681 B2 | 7/2013 | Sutherland et al. |
| 8,496,976 B2 | 7/2013 | Gore et al. |
| 8,512,717 B2 | 8/2013 | Vehige et al. |
| 8,524,777 B2 | 9/2013 | Chang et al. |
| 8,541,463 B2 | 9/2013 | Muller et al. |
| 8,541,466 B2 | 9/2013 | DeLong et al. |
| 8,569,367 B2 | 10/2013 | Vehige et al. |
| 8,569,730 B2 | 10/2013 | Xu et al. |
| 8,586,630 B2 | 11/2013 | Chang et al. |
| 8,592,450 B2 | 11/2013 | Gadek et al. |
| 8,614,293 B2 | 12/2013 | Kaplan et al. |
| 8,629,111 B2 | 1/2014 | Acheampong et al. |
| 8,632,760 B2 | 1/2014 | Woodward et al. |
| 8,633,162 B2 | 1/2014 | Acheampong et al. |
| 8,642,556 B2 | 2/2014 | Acheampong et al. |
| 8,648,048 B2 | 2/2014 | Acheampong et al. |
| 8,648,107 B2 | 2/2014 | Muller et al. |
| 8,664,215 B2 | 3/2014 | Ingerman et al. |
| 8,685,930 B2 | 4/2014 | Acheampong et al. |
| 8,742,069 B2 | 6/2014 | Kaplan et al. |
| 8,748,425 B2 | 6/2014 | Chang et al. |
| 8,772,338 B2 | 7/2014 | Chang et al. |
| 8,858,961 B2 | 10/2014 | Graham et al. |
| 8,906,962 B2 | 12/2014 | deLong et al. |
| 8,927,574 B2 | 1/2015 | Burnier |
| 9,045,457 B2 | 6/2015 | Gadek et al. |
| 9,085,553 B2 | 7/2015 | Zeller et al. |
| 9,216,174 B2 | 12/2015 | Shen et al. |
| 9,248,191 B2 | 2/2016 | Acheampong et al. |
| 9,353,088 B2 | 5/2016 | Burnier |
| 9,394,355 B2 | 7/2016 | Lawrence et al. |
| 9,447,077 B2 | 9/2016 | Burnier et al. |
| 9,907,836 B2* | 3/2018 | Lawrence ............... A23L 33/17 |
| 10,471,128 B2* | 11/2019 | Lawrence ............... A61K 35/64 |
| 2003/0206897 A1 | 11/2003 | O'Prey et al. |
| 2004/0097709 A1 | 5/2004 | Armato et al. |
| 2004/0219630 A1 | 11/2004 | Tsubouchi |
| 2004/0265260 A1 | 12/2004 | Tsubouchi et al. |
| 2005/0143296 A1 | 6/2005 | Tsubouchi et al. |
| 2005/0196370 A1 | 9/2005 | Yu et al. |
| 2005/0202097 A1 | 9/2005 | Maskin |
| 2006/0106104 A1 | 5/2006 | Vehige et al. |
| 2008/0219938 A1 | 9/2008 | Grune |
| 2009/0234026 A1 | 9/2009 | Kaplan et al. |
| 2011/0008406 A1 | 1/2011 | Altman et al. |
| 2011/0105402 A1 | 5/2011 | Kim et al. |
| 2011/0288273 A1 | 11/2011 | Yang et al. |
| 2012/0040907 A1 | 2/2012 | DiBenedetto et al. |
| 2012/0052124 A1 | 3/2012 | Kaplan et al. |
| 2012/0171256 A1 | 7/2012 | Zhang et al. |
| 2013/0039986 A1 | 2/2013 | Kaplan et al. |
| 2013/0060008 A1 | 3/2013 | Wang et al. |
| 2013/0158131 A1 | 6/2013 | Kaplan et al. |
| 2013/0165004 A1 | 6/2013 | Kaplan et al. |
| 2013/0190222 A1 | 7/2013 | Kaplan et al. |
| 2013/0243693 A1 | 9/2013 | Omenetto et al. |
| 2013/0243709 A1 | 9/2013 | Hanson et al. |
| 2014/0193466 A1 | 7/2014 | Lawrence et al. |
| 2014/0235554 A1 | 8/2014 | Lawrence et al. |
| 2015/0093340 A1 | 4/2015 | Altman et al. |
| 2016/0096878 A1 | 4/2016 | Lawrence et al. |
| 2019/0117834 A1* | 4/2019 | Abdel-Naby ......... A61L 27/227 |

FOREIGN PATENT DOCUMENTS

| | | |
|---|---|---|
| CN | 103239707 A | 8/2013 |
| JP | S55124793 A | 9/1980 |
| JP | 0767686 A | 3/1995 |
| JP | H08295697 A | 11/1996 |
| JP | 2000143472 A | 5/2000 |
| WO | 1999033899 A1 | 7/1999 |
| WO | 2007130364 A2 | 11/2007 |
| WO | 2009088119 A1 | 7/2009 |
| WO | 2012170655 A1 | 12/2012 |
| WO | 2013126799 A1 | 8/2013 |
| WO | 2013159101 A1 | 10/2013 |
| WO | 2014145002 A2 | 9/2014 |
| WO | 2014152097 A1 | 9/2014 |
| WO | 2015077300 A1 | 5/2015 |
| WO | 2016100721 A1 | 6/2016 |
| WO | 2017200659 A2 | 11/2017 |

OTHER PUBLICATIONS

Asakura et al., "Possible Implications of Serine and Tyrosine Residues and Intermolecular Interactions on the Appearance of Silk I Structure of Bombyx Mori Silk Fibroin-Derived Synthetic Peptides: High-Resolution 13C Cross-Polarization/Magic-Angle Spinning NMR Study," Biomacromolecules, 6(1):468-474, Jan.-Feb. 2005.

Chon et al., "Silk Fibroin Hydrolysate Inhibits Osteoclastogenesis and Induces Apoptosis of Osteoclasts Derived from RAW 264.7 Cells," Int J Mol Med., 30(5):1203-1210, Nov. 2012.

Daithankar et al., "Moisturizing Efficiency of Silk Protein Hydrolysate: Silk Fibroin," Indian J. Biotech., 4:115-121: Jan. 4, 2005.

Extended Search Report of the European Patent Office dated Apr. 24, 2018 in EP Application No. 15833824.4.6 (EP3182985A1), 7pgs.

Greving et al., "Shear-Induced Self-Assembly of Native Silk Proteins into Fibrils Studied by Atomic Force Microscopy," Biomacromolecules, 13(3):676-682, Feb. 21, 2012.

Hardy et al., "Polymeric Materials Based on Silk Proteins," Polymer, 49(20):4309-4327, Sep. 2008.

Harkin et al., "Silk Fibroin in Ocular Tissue Reconstruction," Biomaterials, 32(10):2445-58, Apr. 2011.

Hashimoto et al., "Quantitative Evaluation of Fibroblast Migration on a Silk Fibroin Surface and TGFBI Gene Expression," J Biomater Sci Polym Ed., 24(2):158-169, Jan. 2013.

International Search Report and Written Opinion of the ISA/US dated Dec. 14, 2015 in International Application No. PCT/US2015/046141, 17pgs.

International Search Report and Written Opinion of the ISA/US dated Dec. 22, 2017 in International Application No. PCT/US2017/026656, 12pgs.

International Search Report and Written Opinion of the ISA/US dated Dec. 4, 2017 in International Application No. PCT/US2017/046659, 11 pgs.

Kang et al., "Preparation and Characterization of Low Molecular Weight Silk Fibroin by High-Temperature and High-Pressure Method," J. Applied Polymer Sci., 85(14):2890-2895, Sep. 2002.

Kaur et al., "Photoprotection by Silk Cocoons," Biomacromolecules, 14(10):3660-3667, Sep. 3, 2013.

Kim et al., "A Transparent Artificial Dura Mater Made of Silk Fibroin as an Inhibitor of Inflammation in Craniotomized Rats," J Neurosurg., 114(2):485-490, Feb. 2011.

(56) References Cited

OTHER PUBLICATIONS

Lawrence et al., "Silk Film Culture System for in vitro Analysis and Biomaterial Design," J Vis Exp., 62:1-6, Apr. 2012.
Matsumoto et al., "Mechanisms of Silk Fibroin Sol-Gel Transitions," J Phys Chem B., 110(43):21630-2638, Nov. 2, 2008.
Patchornik et al., "Nonenzymatic Cleavages of Peptide Chains at the Cysteine and Serine Residues Through Their Conversion Into Dehydroalanine. I. Hydrolytic and Oxidative Cleavage of Dehydroalanine Residues," J. Am. Chem. Soc., 86(6):1206-1212, Mar. 20, 1964.
Rockwood et al., "Materials Fabrication from Bombyx mori Silk Fibroin," Nat Protoc., 6(10):1612-1631, Sep. 2011.
Teng et al., "Physical Crosslinking Modulates Sustained Drug Release from Recombinant Silk-Elastinlike Protein Polymer for Ophthalmic Applications," J. Control Release, 156(2):186-197, Dec. 2011.
Wang et al., "Sonication-Induced Gelation of Silk Fibroin for Cell Encapsulation," Biomaterials, 29(8):1054-1064, Apr. 2008.
Wu et al., "Impact of Sterilization Methods on the Stability of Silk Fibroin Solution," Adv Mater Res., 311-313:1755-1759, Aug. 2011.
Yamada et al., "Preparation of Undegraded Native Molecular Fibroin Solution from Silkworm Cocoons," Mater Sci Eng.: C, 14(1-2):41-46, Aug. 2001.
Zhao et al., "The Effects of Different Sterilization Methods on Silk Fibroin," J Biomed Sci Eng., 4:397-402, May 2011.

\* cited by examiner

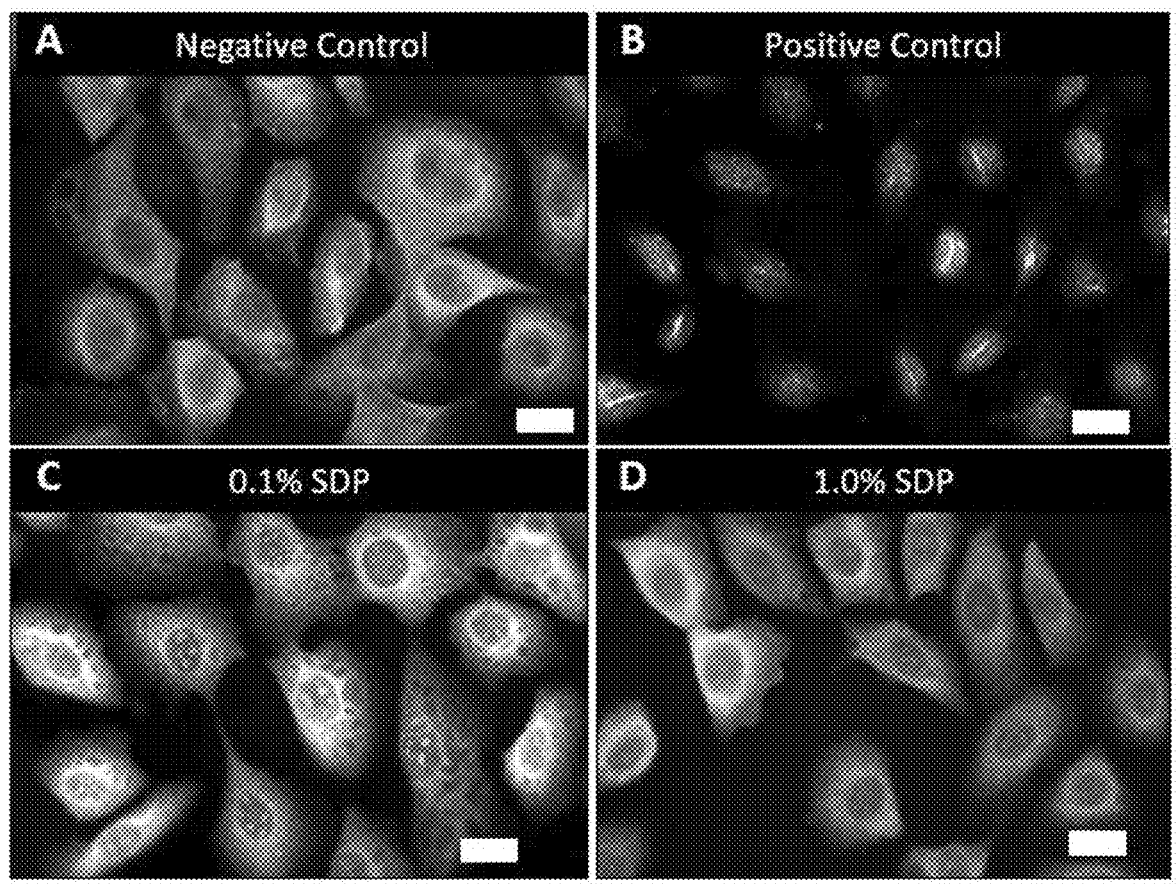
*Fig. 1A-D*
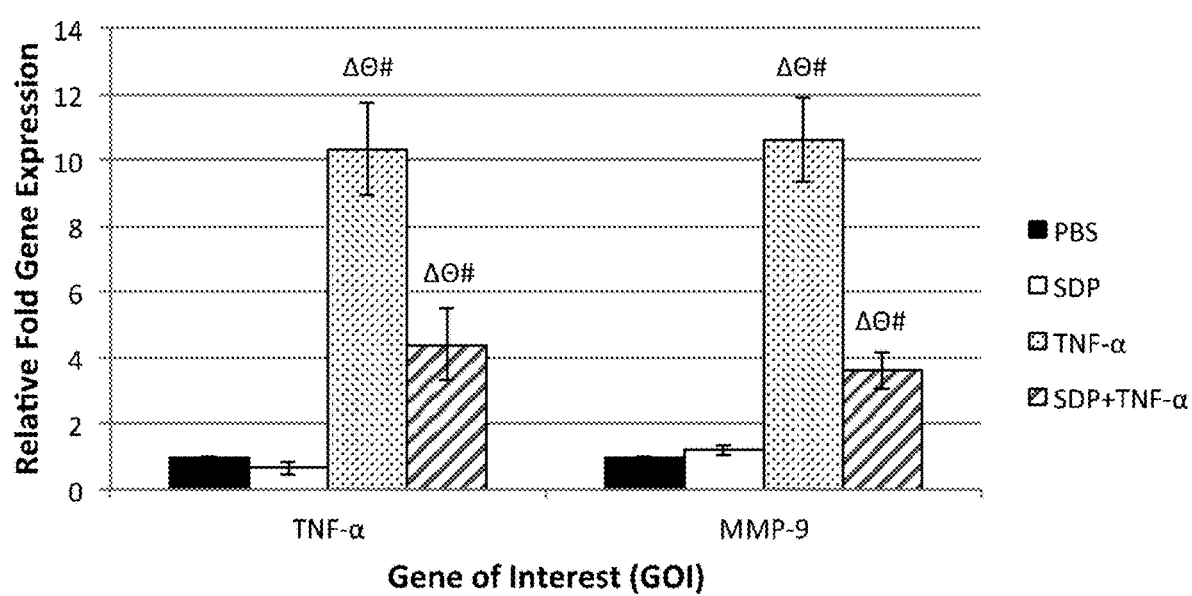
*Fig. 2*

*Fig. 3A-E*

SEQUENCE LISTING

<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ala Gly Ala
1

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aatgtggccg aggactttga ttgc                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aggatggcaa gggacttcct gtaa                                          24

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaggccaagc cctggtatg                                                19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgggccgatt gatctcagc                                                19

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtaccgcta tggttacact cg                                          22

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcagggaca gttgcttct                                              19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctatttggc gctggactt                                              19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcggctcgta gctcttctc                                              19

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgaagaaga acccgtcctc tg                                          22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcatacgtg ccagacaaca cc                                          22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctaccgcttt ccccacttca g                                           21

```
<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcctcagctc cttgatggtc t                                              21
```

SILK-DERIVED PROTEIN FOR TREATING INFLAMMATION

RELATED APPLICATIONS

This application is a national stage entry under 35 U.S.C. § 371 of International Patent Application No. PCT/US2017/046659, filed Aug. 2, 2017, which claims priority under 35 U.S.C. § 119(e) to U.S. Provisional Patent Application Nos. 62/374,532, filed Aug. 12, 2016, 62/407,863, filed Oct. 13, 2016, and 62/467,697, filed Mar. 6, 2017, which applications are incorporated herein by reference.

SEQUENCE LISTING

The instant application contains a Sequence Listing which has been submitted electronically in ASCII format and is hereby incorporated by reference in its entirety. Said ASCII copy, created on Oct. 2, 2017, is named 114_014WO1_SL Sequence Listing and is 3,246 bytes in size.

GOVERNMENT SUPPORT

This invention was made with government support under Grant No. 1152561 awarded by National Science Foundation and Grant No. A151-061-0107 awarded by the United States Army. The government has certain rights in the invention.

BACKGROUND OF THE INVENTION

Inflammation describes the cooperative response of afflicted cells to harmful stimuli (e.g., infection) or local tissue injury in attempt to restore homeostasis. Exposure of resident cells to these aberrant conditions initiates intracellular signaling cascades that result in the production and secretion of inflammatory mediators. Localized deposition of these inflammatory entities serves to recruit immune cells (e.g., neutrophils) from the interstitium and vasculature to the site of injury or insult. Successful removal of the stimulus is followed by tissue repair, which introduces new immune cell types (e.g., macrophages) and signaling intermediaries and concludes the acute inflammatory response (Medzhitov, *Nature*, 2008. 454(7203): 428-435). However, if tissue homeostasis is not achieved within this timespan, a chronic inflammatory response ensues, whereby additional immune cells are introduced to the site of injury in attempt to contain it. Nevertheless, chronic inflammation can permanently undermine the healthy tissue state. Dysregulated signaling pathways that result from chronic inflammation have been implicated in a multitude of diseases, including dry eye, autoimmune disorders, cardiovascular disease, and cancer.

While the instigating cause of the immune response can be foreign to the host, disruption of localized tissue homeostasis due to aberrant cell signaling can also generate concentration gradients of signaling molecules that drive immune cell recruitment and response. For example, disruptions in tear film composition at the apical surface of the eye results in the increased production of proinflammatory cytokines that stimulate the immune cascade both acutely and chronically (Luo et al., *Eye & Contact Lens*, 2005. 31(5): 186-193). This condition, known as keratoconjunctivitis sicca or dry eye syndrome (DES), persists due to a constant inflammatory stimulus that translates into altered cellular mechanical stress (via cell shrinkage) and gene expression (Brocker et al., *Biomolecular Concepts*, 2012. 3(4): 345-364). This further lends to the production of cytokines, which act on the local microenvironment and recruit mediator cell types of the acute inflammatory response. In turn, migratory neutrophils secrete additional pro-inflammatory morphogens that alter ocular limbal vascular permeability and thereby permit influx of activated T cells to the irritated eye surface, transitioning to a chronic inflammatory state (Baudouin, *Survey of Ophthalmology*, 2001. 45(2): S211-220).

One specific example of such a stimulus occurs with tear film fluid hyperosmolarity, which is caused by accelerated tear evaporation or tear gland hyposecretion. If the hyperosmotic stimulus is not addressed by the actions of immune cell mediators, homeostasis is not achieved and destruction of the ocular surface and tear glands evolves over time through dysregulated tissue remodeling mechanisms of the ocular surface. This cascade can lead to the increased production of matrix metalloproteinase 9 (MMP-9) that degrades the ocular surface in a runaway feed-forward mechanism of tissue remodeling.

Approaches to mitigate the inflammatory response typically target the production of pro-inflammatory signaling molecules. These include the use of glucocorticoid steroids, which function to decrease production of proinflammatory proteins while simultaneously increasing production of anti-inflammatory proteins within a recipient cell (Rhen et al., *The New England Journal of Medicine*, 2005. 353(16): 1711-1723). However, the effects of glucocorticoid signaling are potent and not confined to immune cell signaling, with impacts on metabolic and fluid homeostasis, neuronal function, and fetal development. Therefore, glucocorticoid signaling is heavily regulated and generally restricted to chronic hyperactive immune system disorders. Conversely, non-steroidal anti-inflammatory drugs (NSAIDs), which include aspirin, ibuprofen, and naproxen, function to inhibit cyclooxygenase (COX) enzyme activity, which precedes prostaglandin production that is heavily increased in inflamed cells (Ricciotti et al., *Arteriosclerosis, Thrombosis, and Vascular Biology*, 2011. 31(5): 986-1000). NSAIDs are effective combatants of the inflammatory process, but are typically administered systemically and inhibit the functions of COX enzymes elsewhere in the body, which can contribute to stomach ulcerations and renal dysfunction. Given the off-target side effects of the above-mentioned therapeutic strategies, the anti-inflammatory agent ideally should be localized to the injured or infected tissue (e.g., skin, or eye surface).

The application of targeted anti-inflammatory therapies offers promise to attenuate the immune cell response with minimal side effects. For example, the development of antagonist antibodies against pro-inflammatory mediators (e.g., chemokines) has been employed for inflammatory diseases with promising efficacy (Skov et al., *Journal of Immunology*, 2008. 181(1): 669-679). However, the production cost of these proteins is significant and variability in antibody production may influence therapeutic efficacy. Alternatively, pharmacological inhibitors of signaling pathways upstream of chemokine production and/or secretion would be theoretically ideal, since they would eliminate recruitment of immune cell types involved in the acute and eventual chronic inflammatory response. Among these theoretical targets would be the nuclear factor-kappa B (NF-κB) transcription factor family, which is heavily implicated in the production of acute pro-inflammatory morphogens (Hayden et al., *Cell Research*, 2011. 21(2): 223-244). Natively, NF-κB subunits reside in the cytoplasm and are prevented from nuclear translocation by the masking of protein residues that target delivery to this region. However, upon stimulation, the inhibitory protein is quickly degraded, thereby allowing translocation and DNA binding of NF-κB proteins and subsequent gene transcription.

A number of natural and synthetic inhibitors of NF-κB exist. Among the former is silk fibroin, which is a dimer composed of heavy and light protein chains (390 kD and 26 kD, respectively) isolated from the silkworm cocoon (reviewed by Altman et al., *Biomaterials*, 2003. 24(3): 401-416). These globular proteins assemble into a fibrillar architecture by the disulfide linkage of light and heavy chains and exhibit remarkable homogeneity in β-sheet secondary structure. Fibroin has been shown to inhibit transcription and upstream activation (i.e., via inhibition of protein kinases) of NF-κB protein subunits (Chon et al., *International Journal of Molecular Medicine*, 2012. 30(5): 1203-1210). Furthermore, hydrolyzed peptide fragments of fibroin have been shown to inhibit transcription of proinflammatory molecules that are classically under control of NF-κB (Kim et al., *J. Neurosurg.*, 2011. 114(2): 485-90; *J. Microbiol. Biotechnol.*, 2012. 22(4): 494-500). However, the use of silk fibroin has not resulted in effective treatments for inflammatory conditions and wounds.

Furthermore, eye disease and injury remain persistent and serious concerns to the general world population. Ocular disease and trauma pose an immediate threat to normal vision by extending throughout the healing process and risking permanent disability or blindness from prolonged infection, chronic inflammation, and scar formation. As such, there is an immediate need for therapies to reduce inflammation and accelerate healing of the injured or inflamed ocular tissue.

SUMMARY

The invention provides a modified silk fibroin protein for therapeutic applications such as reducing inflammation as well as promoting wound healing and tissue regeneration. The modified protein has been shown to support corneal epithelial cell attachment and proliferation. The silk-derived protein (SDP) described herein is a fibroin-derived protein composition that has reduced beta-sheet activity, resulting in a highly-soluble and aqueous-stable material. SDP can be readily incorporated into solution-based product formulations at high concentrations. Another advantage is that SDP has a high level of miscibility with other dissolved ingredients, such as those typically included in an ophthalmic formulation. One specific use of SDP is its inclusion in ophthalmic formulations as a novel protein component to enhance solution-wetting characteristics on the ocular surface. The SDP can be fractionated and it was surprisingly discovered that low molecular weight fractions of SDP have enhanced anti-inflammatory properties.

The invention therefore provides a fibroin-derived protein composition that possesses enhanced stability in an aqueous solution, wherein the primary amino acid sequences of the fibroin-derived protein composition differ from native fibroin by at least 4% with respect to the absolute values of the combined differences in amino acid content of serine, glycine, and alanine; cysteine disulfide bonds between the fibroin heavy and fibroin light protein chains of fibroin are reduced or eliminated; a plurality of peptide chains in the protein composition terminate in amide (—C(=O)NH$_2$) groups; the composition has a serine content that is reduced by greater than 25% compared to native fibroin protein, wherein the serine content is at least about 5%; and wherein the average molecular weight of the fibroin-derived protein composition is less than 40 kDa and greater than 2 kDa.

In some embodiments, greater than 50% of the protein chains of the protein composition have a molecular weight within the range of 10 kDa to 60 kDa. In various embodiments, the protein composition does not gel upon sonication of an aqueous solution of the protein composition at concentrations of up to 10% w/w.

The protein composition can have less than 8% serine, less than 7% serine, or less than 6% serine amino acid residues. The protein composition can have greater than 46% glycine amino acids, greater than 46.5% glycine amino acids. The protein can have greater than 30% alanine amino acids, or greater than 30.5% alanine amino acids.

The protein composition can completely re-dissolves in water after being dried to a thin film. Beta-sheet protein structures are minimal or absent in aqueous solution. The protein composition can maintain an optical absorbance in aqueous solution of less than 0.25 at 550 nm after at least five seconds of sonication.

The invention also provides an ophthalmic formulation comprising the protein composition described herein, and water, and optionally one or more of a buffering medium, a salt, a stabilizer, a preservative, and a lubricant.

The invention further provides a method for reducing inflammation comprising administering a fibroin-derived protein composition to inflamed tissue; wherein the primary amino acid sequences of the fibroin-derived protein composition differ from native fibroin by at least 4% with respect to the absolute value of the combined differences in amino acid content of serine, glycine, and alanine; cysteine disulfide bonds between the fibroin heavy and fibroin light protein chains of fibroin are reduced or eliminated; a plurality of peptide chains in the protein composition terminate in amide (—C(=O)NH$_2$) groups; the composition has a serine content that is reduced by greater than 25% compared to native fibroin protein, and wherein the serine content is at least about 5%; and wherein the average molecular weight of the fibroin-derived protein composition is less than 60 kDa and greater than 2 kDa; thereby reducing transcription factor signaling within cell nuclei of the tissue, thereby reducing the inflammation. The average molecular weight of the fibroin-derived protein composition can also be less than 55 kDa, and/or greater than about 5 kDa, greater than 10 kDa, greater than 15 kDa, or greater than 20 kDa.

The administration to inflamed tissue can reduce transcription of one or more of the inflammatory genes TNF-α, MMP-9, IL-1β, and IL-6. The reduction can be as much as 20%, 40%, 50%, or 60% compared to in absence of the protein composition. The administration can be to the cornea and the administration can reduce the presence of MMP-9 in the cornea. The administration can be to the eye and the administration reduces inflammation on the ocular surface, for example, as determined by ELISA measurement of proinflammatory markers in the tear film. The reduction in inflammation can be accompanied by an increase in cell migration rates at the point of inflammation, for example, an increase in cell proliferation, as determined by an MTT assay.

The protein composition can have an average molecular weight less than 40 kDa, or less than 35 kDa. The fibroin-derived protein composition can be dissolved in an ophthalmic formulation comprising one or more of a buffering medium, a salt, a stabilizer, a preservative, and a lubricant.

The inflammation can be inflammation caused by an ocular condition, wherein the ocular condition is dry eye syndrome, corneal ulcer, corneal erosion, corneal abrasion, corneal degeneration, corneal perforation, corneal scarring, epithelial defect, keratoconjunctivitis, idiopathic uveitis, corneal transplantation, age-related macular degeneration, diabetic eye, blepharitis, glaucoma, ocular hypertension, post-operative eye pain and inflammation, posterior segment neovascularization, proliferative vitreoretinopathy, cytomegalovirus retinitis, endophthalmitis, choroidal neovascular membrane, vascular occlusive disease, allergic eye disease, tumor, retinitis pigmentosa, eye infection, scleritis, ptosis, miosis, eye pain, mydriasis, neuralgia, cicatrizing ocular surface disease, ocular infection, inflammatory ocular disease, ocular surface disease, corneal disease, retinal disease, ocular manifestations of systemic diseases, hereditary eye condition, ocular tumor, increased intraocular pressure, herpetic infection, ptyrigium or scleral tumor, wound sustained to ocular surface, post-photorefractive keratotomy eye pain and inflammation, thermal or chemical burn to the cornea, scleral wound, or keratoconus and conjunctival wound. In one embodiment, the inflammation is caused by dry eye syndrome.

The invention further provides for the use of a fibroin-derived protein composition described herein for treating inflammation, wherein the primary amino acid sequences of the fibroin-derived protein composition differ from native fibroin by at least 4% with respect to the absolute value of the combined differences in amino acid content of serine, glycine, and alanine; cysteine disulfide bonds between the fibroin heavy and fibroin light protein chains of fibroin are reduced or eliminated; a plurality of peptide chains in the protein composition terminate in amide (—C(=O)NH$_2$) groups; the composition has a serine content that is reduced by greater than 25% compared to native fibroin protein, and wherein the serine content is at least about 5%; and wherein the average molecular weight of the fibroin-derived protein composition is less than 60 kDa and greater than 10 kDa. The protein composition can have an average molecular weight less than 35 kDa. The composition can be a composition for the treatment of dry eye syndrome.

Accordingly, SDP compositions are provided herein that possess enhanced stability in aqueous solutions in which the primary amino acid sequence of native fibroin is modified from native silk fibroin, wherein cysteine disulfide bonds between the fibroin heavy and fibroin light protein chains reduced or eliminated; wherein the composition has a serine content that is reduced by greater than 40% compared to native fibroin protein; and wherein the average molecular weight of the SDP is less than about 60 kDa.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1A-D. p65 protein immunostaining (white) of hCLE cultures for NF-κB activation. (A) Negative control cultures treated with PBS showed cytosolic p65 staining indicating native NF-κB inactivity. (B) Positive control cultures treated with PBS containing 1 ng/mL TNF-α demonstrated punctate p65 nuclear staining indicating protein translocation and hence a high level of NF-κB activation. (C and D) Culture treated with PBS, TNF-α, and 0.1% SDP or 1% SDP demonstrated a dose-dependent reduction in nuclear p65 staining indicating higher SDP concentrations inhibit NF-κB activation to a greater extent, respectively. (Scale bars=20 µm).

FIG. 2. Summary qPCR results of relative fold gene expression for TNF-α and MMP-9 for hCLE cultures treated with PBS, PBS plus 0.5% SDP, PBS plus 1 ng/mL TNF-α cytokine, and PBS plus 1 ng/mL TNF-α cytokine plus 0.5% SDP. TNF-α and MMP-9 are known genetic markers of NF-κB activation. Cultures stimulated with TNF-α and treated with 0.5% SDP were found to have a 6-fold reduction in gene expression relative to TNF-α cytokine stimulated controls (Δ $p<0.01$ compared to PBS for respective GOI; Θ $p<0.01$ vs. SDP for respective GOI; and # $p<0.05$ vs. indicated groups; n=3).

DETAILED DESCRIPTION OF THE INVENTION

The invention provides protein compositions derived from SDP for treating inflammation and for treating wounds. Evidence supports that proteins isolated from the silkworm cocoon stimulate growth of corneal cells and alter expression of genes implicated in wound healing and inflammation (FIGS. 1-5). The protein compositions described herein also possess enhanced solubility and stability in aqueous solutions. Methods of making protein compositions include modifying the primary amino acid sequence of native fibroin such that cysteine disulfide bonds between the fibroin heavy and fibroin light protein chains are reduced or eliminated. Additionally, the serine content of the protein composition is reduced by greater than 40% compared to native fibroin protein, and the average weight molecular weight of the proteins is less than about 60 kDa. In some cases, protein compositions described herein include or be derived from the protein compositions described in U.S. Pat. No. 9,394,355, the entire disclosure of which is hereby incorporated by reference into this specification. Lower average molecular weight fractions can also be isolated to provide compositions with enhanced anti-inflammatory activity by virtue of their enhanced ability to reduce the expression of pro-inflammatory genes compared to larger molecular weight fractions or the SDP composition in its entirety.

Figure 6:
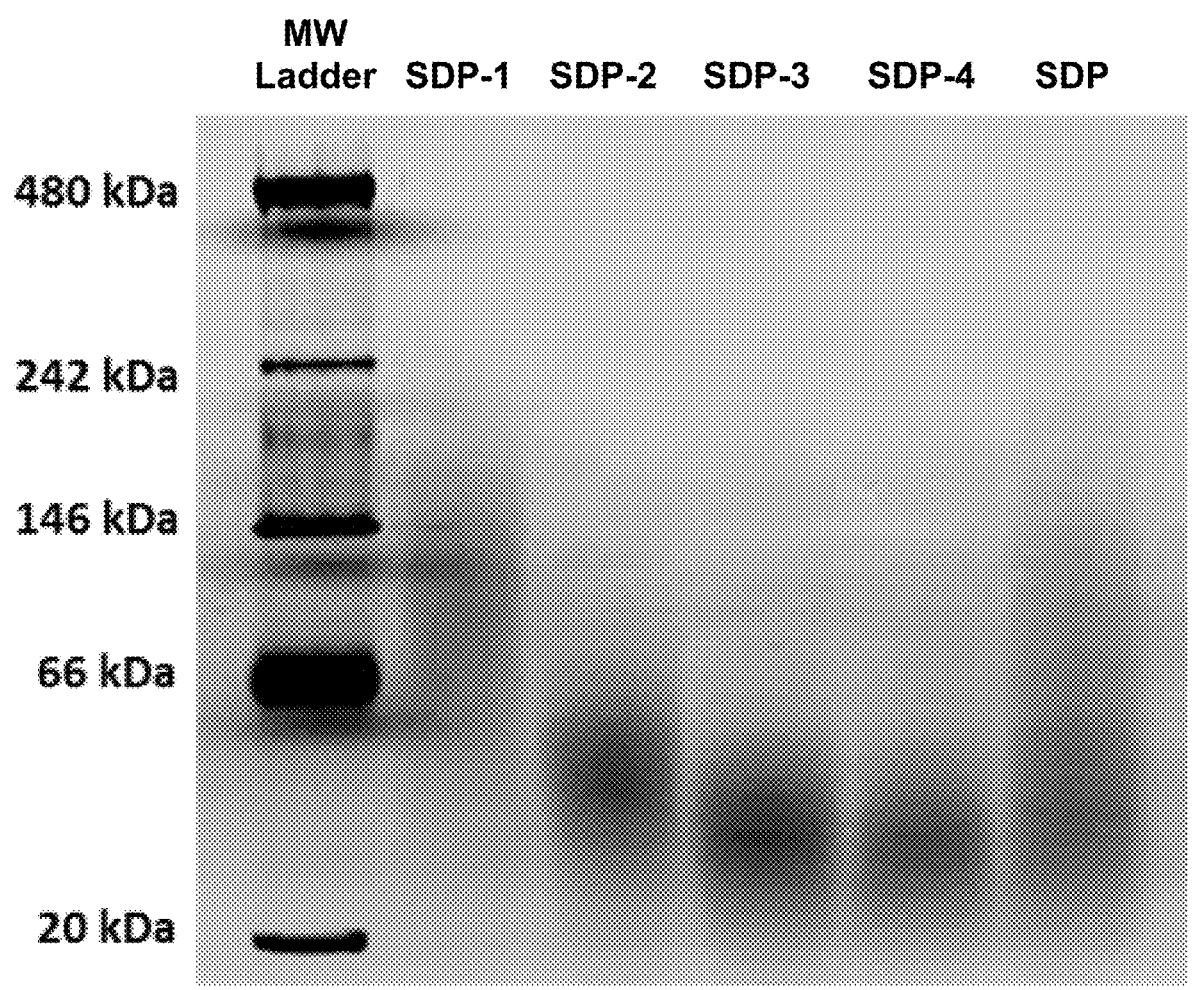
FIG. 6. SDS-PAGE lanes 2-5 represent the respective molecular weight (MW) distributions of SEC-fractionated SDP populations for which biological impact was evaluated (SDP-1, SDP-2, SDP-3, SDP-4, and SDP). Lane 6 illustrates the non-fractionated SDP distribution from which fractions were derived. MW standards are shown in lane 1.

Discrete SDP subpopulations further enhance healing and reduce inflammation in the body, particularly in corneal tissue. Selected SDP fractions have been shown to enhance the effective potency of SDP on cell migration response and inflammation. The SDP fractions were prepared by extracting Bombyx mori silkworm cocoons fibers in 0.3% sodium carbonate at 95° C., and then fibroin fiber was dissolved in 54% LiBr solution. The dissolved solution was autoclaved, coarse filtered, and then purified by diafiltration. The material was then filtered through a nominal polypropylene filter to produce a final SDP solution. The SDP solution was then separated by molecular weight (MW) through the use of one of two methods depending on the specific experiment. In the first method, centrifugation using molecular weight cutoff filters was utilized to separate out SDP protein fractions by molecular weight cutoff (MWCO) size. For example, SDP can be centrifuged at 5000×g until samples are reduced to 10% of starting volume (e.g., 15 mL initial volume concentrated to 1.5 mL, for certain experiments described herein). Proteins sieved through the filter are less than the molecular MWCO of a particular filter; the retained proteins are generally of equal or greater molecular weight. In a second method, sample SDP fractions can also be isolated by size exclusion chromatography (SEC) to produce discrete protein sub-populations, or fractions. Four fractions of decreasing average molecular weight were produced and are referred to as SDP-1, SDP-2, SDP-3, and SDP-4 (FIG. 6).

The two smallest molecular weight SDP fractions, SDP-3 and SDP-4, significantly reduce inflammation and enhance wound healing of hCLE cultures in vitro through increased cell migration and proliferation effects (FIG. 7-12). These SDP fractions inhibit inflammatory signaling, which can further enhance wound healing and improve long-term patient outcomes. The protein fractions derived from SDP can therefore be used for treating inflammation and related conditions. One specific therapeutic application is in the treatment of dry eye disease, which is known to be an inflammatory related disease that is driven, in part, by the NF-κB signaling pathway, which is inhibited by SDP. In another specific therapeutic application, SDP may be utilized to treat post-surgical injuries to induce enhanced healing outcomes by reducing inflammation and/or increasing cell proliferation and/or migration, such as those injuries produced during refractive eye surgery or cataract removal, and/or accidental injuries where the corneal epithelium is compromised.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a component" includes a plurality of such components, so that a component X includes a plurality of components X. It is further noted that the claims may be drafted to exclude an optional element. As such, this statement is intended to serve as antecedent basis for the use of exclusive terminology, such as "solely," "only," "other than", and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

The term "about" can refer to a variation of ±5%, +10%, +20%, or +25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, element, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, an invention encompasses not only the entire group listed as a whole, but each member of the group individually and all possible subgroups of the main group. Additionally, for all purposes, an invention encompasses not only the main group, but also the main group absent one or more of the group members. An invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

For a therapeutic application, an "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is within the capacity of persons skilled in the art. The term "effective amount" is intended to include an amount of a composition described herein, or an amount of a combination of peptides described herein, e.g., that is effective to treat or prevent a disease or disorder, or to treat the symptoms of the disease or disorder, in a host. Thus, an "effective amount" generally means an amount that provides the desired effect.

Fibroin is a protein derived from the silkworm cocoon (e.g., *Bombyx mori*). Fibroin includes a heavy chain that is about 350-400 kDa in molecular weight and a light chain that is about 24-27 kDa in molecular weight, wherein the heavy and light chains are linked together by a disulfide bond. The primary sequences of the heavy and light chains are known in the art. The fibroin protein chains possess hydrophilic N and C terminal domains, and alternating blocks of hydrophobic/hydrophilic amino acid sequences allowing for a mixture of steric and electrostatic interactions with surrounding molecules in solution. At low concentration dilutions (1% or less) the fibroin protein molecule is known to take on an extended protein chain form and not immediately aggregate in solution. The fibroin protein is highly miscible with hydrating molecules such as HA, PEG, glycerin, and CMC, has been found to be highly biocompatible, and integrates or degrades naturally within the body through enzymatic action. Native fibroin, or also referred to herein as prior art silk fibroin (PASF), is known in the art and has been described by, for example, Daithankar et al. (*Indian J Biotechnol*. 2005, 4, 115-121) and International Publication No. WO 2014/145002 (Kluge et al.).

The terms "silk-derived protein" (SDP) and "fibroin-derived protein" are used interchangeably herein. These materials are prepared by the processes described herein involving heat, pressure, and a high concentration of a heavy salt solution. Therefore 'silk-derived' and 'fibroin-derived' refer to the starting material of the process that structurally modifies the silk fibroin protein to arrive at a protein composition (SDP) with the structural, chemical and physical properties described herein. The SDP compositions possess enhanced solubility and stability in an aqueous solution. The SDP may be derived from silkworm silk (e.g., *Bombyx mori*), spider silk, or genetically engineered silk.

As used herein, the terms "molecular weight" and "average molecular weight" refer to weight average molecular weight determined by standard Sodium Dodecyl Sulfate Polyacrylamide Gel Electrophoresis (SDS-PAGE) electrophoresis methods undertaken with a NuPAGE™ 4%-12%

Bis-Tris protein gel (ThermoFisher Scientific, Inc.) in combination analysis with ImageJ software (National Institutes of Health). ImageJ is used to determine the relative amount of protein of a given molecular weight in a sample. The software accomplishes this by translating the staining on the gel (i.e., the amount of protein) into a quantitative signal intensity. The user then compares this signal to a standard (or ladder) consisting of species of known molecular weights. The amount of signal between each marker on the ladder is divided by the whole signal. The cumulative summation of each protein sub-population, also referred to herein as fractions and interchangeably also referred to as fragments, allows the user to determine the median molecular weight, which is referred to herein as the average molecular weight. In practice, electrophoresis gels are stained, and then scanned into greyscale images, which are converted into histograms using ImageJ. Total pixel intensity within each gel lane is quantified by ImageJ (i.e., total area under the histogram), and subsequently fractionated into populations demarcated by protein molecular weight standards also stained on the gel. The histogram pixel area between any two molecular weight standards is divided by the total histogram area of the protein, thereby providing the fraction of total protein that falls within these molecular weights. Analysis by other methods may provide different values that account for certain peptides that are not accounted for by SDS-PAGE methods. For example, HPLC can be used to analyze the average molecular weights, which method provides values that are typically about 10-30%, lower than determined by SDS-PAGE (increasing differences as molecular weights decrease).

Preparation of SDP Compositions

SDP compositions described herein can possess enhanced stability compared to native fibroin in aqueous solutions. The enhanced stability achieved by the SDP compositions provided herein, which is also referred herein as a SDP, allow the material to remain in solution significantly longer than the native/PASF proteins (referred to herein as PASF). Enhanced stability of the SDP materials provided herein also allow for the preparation of SDP solutions of high concentration without aggregation, precipitation, or gelation. In commercial applications such as eye drops or applications requiring protein to be soluble in solution, enhanced stability can provide suitably lengthy shelf life and increased quality of the product by reducing protein aggregation. Potential aggregation of protein in solution can negatively impact a product's desired performance for a particular application. This is especially true for eye drop formulations given that aggregates could cause abrasive damage to the ocular surface. The ability to concentrate the SDP to high constitutions in solution (over 50% w/v or >500 mg/mL) is significantly advantageous for inventorying a useful working solution that can be used as-is or diluted for any number of applications. Examples of such applications are the use of SDP as an ingredient in ophthalmic formulations, such as those provided herein, as a protein supplement or additive.

Transforming the primary amino acid sequences of the native fibroin protein into the SDP material may enhance its stability in aqueous solutions by decreasing the susceptibility of the molecules to aggregate. Aggregation eventually leads to gel formation. In the transformation of the native fibroin, both serine and cysteine amino acids are cleaved in the presence of high heat and dehydrating conditions. Similarly, Patchornik et al. (J. Am. Chem. Soc. 1964, 86, 1206) demonstrated that a dehydroalanine (DHA) intermediate is formed from serine and cysteine in solution. The amino acid degradation is further driven when in the presence of a strong dehydrating solvent system, such as the 50-55% w/v LiBr solution as described herein, in which a hydride shift takes place to induce removal of water. The degradation reaction can take place in the presence of hydroxide ions (e.g., pH 7.5 to pH 11), which further drives cleavage of the DHA intermediate. This cleavage forms an amide, a pyruvoyl peptide, and LiBr. One viable chemical mechanism is outlined in Scheme 1 for a serine amino acid, which scheme is also applicable for cysteine amino acids. Chemical alteration of the serine and cysteine amino acids of the PASF protein into a DHA intermediate with further hydrolytic cleavage leads to enhanced solution stability of the SDP products.

Scheme 1. Schematic of an underlying chemical reaction for serine and cysteine degradation.

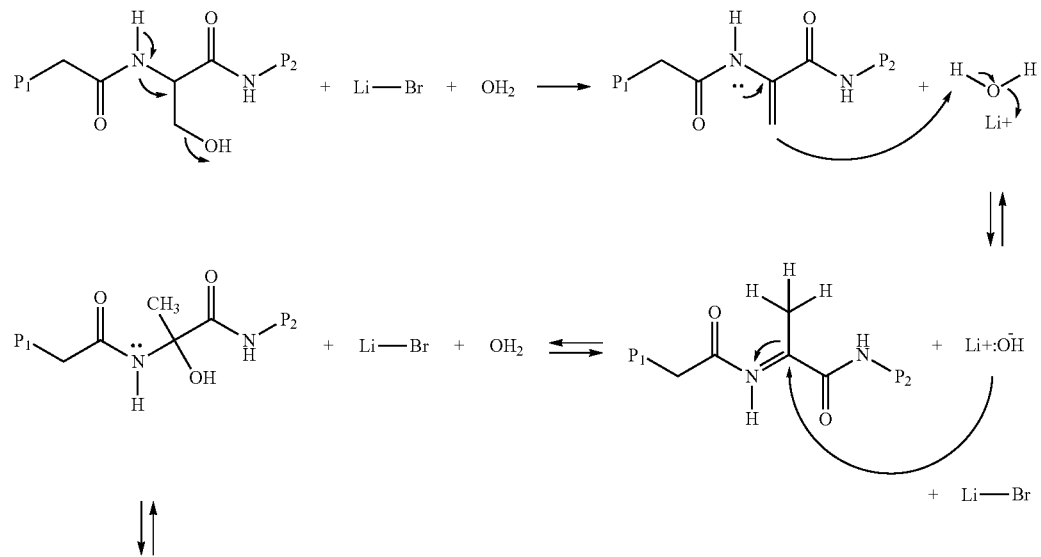

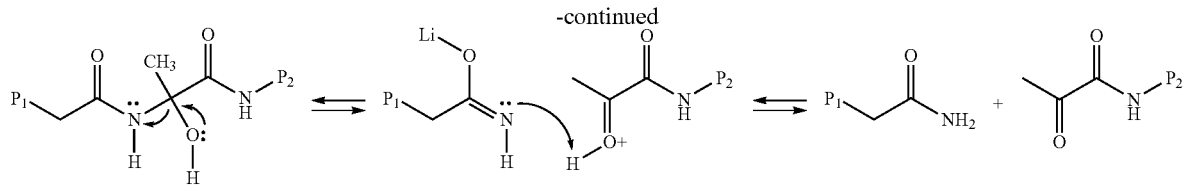
-continued

Degradation is driven by the production of a DHA intermediate that is formed from a hydride shift reaction in the presence of a dehydrating high salt concentration environment. Degradation of DHA is then accomplished through an $SN_2$ reaction within the basic solvent environment.

This cleavage reaction discussed above can significantly affect macromolecular properties of the resulting peptides, which results in an aqueous solution of stabilized SDP material. The initial protein aggregation of fibroin is believed to be instigated by interactions of the native fibroin heavy and light chains at the cysteine amino acids as described by Greving et al. (*Biomacromolecules* 2012, 13(3): 676-682). The cysteine amino acids within the fibroin light and heavy protein chains interact with one another through disulfide linkages. These disulfide bridges participate in fibroin protein aggregation and gel network flocculation. Without the native fibroin light chain present, the proteins are significantly less susceptible to aggregation. Therefore, the process described herein can effectively reduce\the native fibroin light chain's ability to form disulfide bonds by reducing cysteine content and thus reducing or eliminating disulfide bond-forming capability. Through this mechanism, the transformative process described herein functionally stabilizes the resulting SDP in solution by reducing or eliminating the ability to form cysteine-derived aggregations.

In addition to aggregation-inducing disulfide bridges, the susceptibility of the silk fibroin to further aggregate into flocculated structure is also driven by the protein's amino acid chemistry as described by Mayen et al. (*Biophysical Chemistry* 2015, 197:10-17). Molecular modeling of silk fibroin serine, alanine, and glycine amino acid sequences have shown that the presence of serine enhances initial protein-to-protein interaction through a greater propensity to create hydrogen bonding between adjacent fibroin protein chain moieties. The models demonstrate that reduced serine and increased alanine and glycine decrease the initial propensity for protein aggregation. The molecular modeling observations indicate that by altering the native amino acid chemistry of the fibroin protein a material could be generated that would have higher stability in aqueous solution.

One strategy to accomplish enhanced stability is to eliminate charged functional groups, such as hydroxyls, from the protein. Due to the relatively high electronegativity of hydroxyl groups, this chemistry can drive both hydrogen bonding with available hydrogen atoms and non-specific charge interactions with positively charged amino acid groups. Almost 12% of the native fibroin protein's content is composed of serine, which bears a hydroxyl functional group. Therefore, by reducing the availability of hydroxyl groups that facilitate hydrogen bonding, the overall protein stability in solution may be enhanced. The process described herein effectively reduces the amount of serine content and increases the relative alanine and glycine content, which eliminates the number of available hydroxyl groups available to create hydrogen bonds. Through this mechanism the process described herein functionally stabilizes the resulting SDP in solution extended periods of time (e.g., at least several [6-8] months, and/or for more than 1.5 years; extended studies are ongoing, indicating that stability may be maintained for more than 2 years, or more than 3 years).

In addition to the reduction of cysteine and serine moieties, solvent charge interaction is important for stabilizing a protein solution. After initial protein flocculation, the gelation process is believed to continue to drive closer associations among the native fibroin heavy chains, which leads to both intra- and inter-molecular beta-sheet formation among hydrophobic blocks of the heavy chains. Once significant beta-sheet formation occurs, the fibroin solution transitions to a gel. As the solution transitions to a gel, and the fibroin becomes insoluble and is no longer useful as a solution-based product. To prevent gelation, the pH of the SDP solution can be raised to high alkalinity to enhance stability, for example over a pH of 7.5. As a result, the increased pH produces additional free hydroxyl groups that form a valence shield around the SDP molecules in solution. The formed valence shield acts to produce a zeta potential that stabilizes the protein by reducing protein-protein interactions derived from hydrogen bonding or non-specific charged and/or hydrophobic interactions. The fibroin-transformation process functionally stabilizes processed SDP in solution through this mechanism and others. The SDP can be derived from *Bombyx mori* silkworm fibroin or other fibroin from the *Bombyx* genus or other silk proteins.

SDP material can be prepared by the following process.

1. Silk cocoons are prepared by removing pupae material and pre-rinsing in warm water.

2. Native fibroin protein fibers are extracted from the gum-like sericin proteins by washing the cocoons in water at high water temperature, typically 95° C. or more, at alkaline pH.

3. The extracted fibroin fibers are dried and then dissolved using a solvent system that neutralizes hydrogen bonding between the beta-sheets; a 54% LiBr aqueous solution of 20% w/v silk fibroin protein is effective for this neutralization step.

4. The fibroin protein dissolved in LiBr solution is processed in an autoclave environment (~121° C. [~250° F.], at ~15-17 PSI pressure, for approximately 30 minutes at temperature).

5. The heat-processed fibroin protein and LiBr solution are then dialyzed to remove lithium and bromide ions from the solution. At this point in the process the material has been chemically transformed to SDP.

6. The dialyzed SDP is then filtered to remove any non-dissolved aggregates and contaminating bioburden.

The SDP solution is produced using a distinctly different process than the process used for current silk fibroin solution production. Notably, the autoclaving of the silk fibroin protein while it is combined with LiBr in solution initiates chemical transitions to produce the stabilized SDP material. The fibroin protein is dissolved in LiBr solution, which neutralizes hydrogen bonding and electrostatic interactions of the solubilized native fibroin protein. This leaves the protein without specific secondary structure confirmations in solution. As a result, the thermodynamic energy required to hydrolyze covalent bonding within the fibroin protein chain is at its lowest energy requirements to initiate hydrolytic cleavage.

In one embodiment, the temperature is set to 121° C. for 30 minutes at 15-17 PSI autoclave conditions. However, in various embodiments, the processing conditions may be modified to stabilize the SDP material to varying degrees. In other embodiments, additional protein solubilization agents can be used in the process, including other or additional halide salts such as calcium chloride and sodium thiocyanate, organic agents such as urea, guanidine hydrochloride, and 1,1,1,3,3,3-hexafluoroisopropanol, additional strong ionic liquid solution additives such as calcium nitrate and 1-butyl-3-methylimidazolium chloride, or a combination thereof.

SDP Compositions

Protein composition described herein can be derived from silk fibroin and possess enhanced solubility and stability in aqueous solutions. The compositions can be used to treat and reduce inflammation. In one embodiment, the SDP and/or fractions thereof have primary amino acid sequences that differ from native fibroin by at least 4% (via summation of the absolute values of the differences) with respect to the combined amino acid content of serine, glycine, and alanine. A plurality of the protein fragments of SDP can terminate in amide (—C(=O)NH$_2$) groups. SDP can have a serine content that is reduced by greater than 40% compared to native fibroin, wherein the serine content is at least about 5%. The cysteine disulfide bonds between the fibroin heavy and fibroin light protein chains of fibroin may be reduced or eliminated. The SDP compositions provided herein possess enhanced stability in an aqueous solution. In certain embodiments, at least 75 percent of the protein fragments have a molecular weight of less than about 60 kDa and act as an anti-inflammatory that also promotes cell migration and proliferation in the tissue to close the wound. The composition may comprise less than 8.5% serine amino acid residues. In some embodiments, the average molecular weight of the SDP is less than 55 kDa.

In some cases, protein compositions provided herein are prepared by a process comprising heating an aqueous fibroin solution at an elevated pressure. The aqueous fibroin solution includes lithium bromide at a concentration of at least 8M. The aqueous fibroin solution is heated to at least about 105° C. (221° F.) under a pressure of at least about 10 PSI for at least about 20 minutes, to provide the protein composition. As a result of these processing conditions, the polypeptides of the protein composition comprise less than 8.5% serine amino acid residues, and a plurality of the protein fragments terminate in amide (C(=O)NH$_2$) groups.

In some cases, protein compositions provided herein are prepared by a process comprising heating an aqueous fibroin solution at an elevated pressure, wherein the aqueous fibroin solution comprises lithium bromide at a concentration of 9-10M, and wherein the aqueous fibroin solution is heated to a temperature in the range of about 115° C. (239° F.) to about 125° C. (257° F.), under a pressure of about 15 PSI to about 20 PSI for at least about 20 minutes; to provide the protein composition. The protein composition can include less than 6.5% serine amino acid residues.

SDP compositions provided herein can possess enhanced stability in aqueous solution, wherein: the primary amino acid sequences of the SDP composition differs from native fibroin by at least 4% with respect to the combined (absolute value) difference in serine, glycine, and alanine content (SDP vs. PASF); cysteine disulfide bonds between the fibroin heavy and fibroin light protein chains are reduced or eliminated; and the composition has a serine content that is reduced by greater than 25% compared to native fibroin protein. The average molecular weight of the SDP composition can be less than about 60 kDa and greater than about 2 kDa, or greater than about 10 kDa, as determined by the MWCO of the dialyzing membrane and SDS-PAGE analysis.

In some cases, SDP compositions provided herein possess enhanced stability in aqueous solution, wherein: the primary amino acid sequences of the SDP composition differs from native fibroin by at least 6% with respect to the combined difference in serine, glycine, and alanine content; cysteine disulfide bonds between the fibroin heavy and fibroin light protein chains are reduced or eliminated; and the composition has a serine content that is reduced by greater than 40% compared to native fibroin protein. The average molecular weight of the SDP composition can be less than about 55 kDa and greater than about 10 kDa, as determined by the MWCO of the dialyzing membrane and SDS-PAGE analysis.

In some cases, SDP compositions provided herein possess enhanced stability in aqueous solutions, wherein: the primary amino acid sequences of the SDP composition is modified from native silk fibroin; cysteine disulfide bonds between the fibroin heavy and fibroin light protein chains are reduced or eliminated; the average molecular weight of the SDP composition is less than about 60 kDa and greater than about 10 kDa; and a 5% w/w aqueous solution of the SDP composition maintains an optical absorbance at 550 nm of less than 0.25 for at least two hours after five seconds of sonication.

In some cases, SDP compositions provided herein possess enhanced stability in aqueous solutions, wherein: the primary amino acid sequences of the SDP composition is modified from native silk fibroin such that they differ from native fibroin by at least 5% with respect to the combined (absolute value) difference in serine, glycine, and alanine content. In some embodiments, the difference of is at least 6%, 8%, 10%, 12% or 14% compared to native fibroin. Cysteine disulfide bonds between the fibroin heavy and fibroin light protein chains are reduced or eliminated; the average molecular weight of the SDP composition is less than about 60 kDa and greater than about 15 kDa; and the SDP composition maintains an optical absorbance at 550 nm of less than 0.2 for at least two hours after five seconds of sonication.

In some cases, SDP compositions provided herein can be isolated and/or purified as a dry powder or film, for example, by dialysis and/or filtration. Alternatively, SDP compositions provided herein can be isolated and/or purified as a stable aqueous solution, which can be modified for use as a therapeutic formulation, such as an ophthalmic formulation.

In various embodiments, the amino acid compositions of the SDP found in protein compositions provided herein can differ from the amino acid composition of native fibroin by at least 4%, by at least 4.5%, by at least 5%, or by at least 5.5%, or by at least 6%, with respect to the content of serine, glycine, and alanine combined.

In some cases, protein compositions described herein have a serine content that is reduced by greater than 25%, by greater than 30%, by greater than 35%, by greater than 40%, or by greater than 45%, compared to the serine content of native fibroin protein.

The average molecular weight of SDP compositions provided herein can be less than about 80 kDa, less than about 70 kDa, less than about 60 kDa, or less than about 55 kDa, or the composition has an average molecular weight of about 50-60 kDa, or about 51-55 kDa. In various embodiments, the average molecular weight of the SDP composition can be greater than about 2 kDa, greater than about 10 kDa, greater than about 15 kDa, greater than about 20 kDa, greater than about 25 kDa, greater than about 30 kDa, greater than about 35 kDa, greater than about 40 kDa, or greater than about 50 kDa. Accordingly, the (weight average) average molecular weight of SDP compositions provided herein can be about 5 kDa to about 80 kDa, about 10 kDa to about 65 kDa, about 15 kDa to about 60 kDa, about 15 kDa to about 60 kDa, about 20 kDa to about 65 kDa, about 20 kDa to about 55 kDa. In various embodiments, the average molecular weight of the SDP composition is about 45 kDa to about 65 kDa, about 45 kDa to about 60 kDa, about 50 kDa to about 65 kDa, or about 50 kDa to about 60 kDa.

The SDP protein compositions can be soluble in water at 40% w/w without any precipitation observable by ocular inspection.

In some embodiments, protein compositions provided herein comprise less than 8% serine amino acid residues. In some cases, protein compositions provided herein comprise less than 7.5% serine amino acid residues, less than 7% serine amino acid residues, less than 6.5% serine amino acid residues, or less than 6% serine amino acid residues. The serine content of the peptide compositions is generally at least about 4%, or at least about 5%, or about 4-5%.

In some embodiments, protein compositions provided herein comprise greater than 46.5% glycine amino acids, relative to the total amino acid content of the protein composition. In some cases, protein compositions provided herein comprise greater than 47% glycine amino acids, greater than 47.5% glycine amino acids, or greater than 48% glycine amino acids.

In some embodiments, protein compositions provided herein comprise greater than 30% alanine amino acids, relative to the total amino acid content of the protein composition. In some cases, protein compositions provided herein comprise greater than 30.5% alanine, greater than 31% alanine, or greater than 31.5% alanine.

In some embodiments, protein compositions provided herein can completely re-dissolve after being dried to a thin film. In various embodiments, protein compositions provided herein can lack beta-sheet protein structure in aqueous solution. The protein composition can maintain an optical absorbance in aqueous solution of less than 0.25 at 550 nm after at least five seconds of sonication.

In some embodiments, protein compositions provided herein can be in combination with water. In some cases, protein compositions provided herein can completely dissolve in water at a concentration of 10% w/w, or even greater concentrations such as 15% w/w, 20% w/w, 25% w/w, 30% w/w, 35% w/w, or 40% w/w. In some embodiments, protein compositions provided herein can be isolated and purified, for example, by dialysis, filtration, or a combination thereof.

In various embodiments, protein compositions provided herein can enhance the spreading of an aqueous solution comprising the protein composition and ophthalmic formulation components, for example, compared to the spreading of a corresponding composition that does not include the protein composition. This enhanced spreading can result in an increase in surface area of the aqueous solution by greater than twofold, or greater than threefold.

In various embodiments, the SDP protein compositions do not form a gel at concentrations up to 20% w/v, up to 30% w/v, or up to 40% w/v in water. In some embodiments, SDP compositions provided herein can have glycine-alanine-glycine-alanine (GAGA) (SEQ ID NO: 1) segments of amino acids that comprise at least about 47.5% of the amino acids of the SDP composition. In some cases, SDP compositions provided herein can also have GAGA (SEQ ID NO: 1) segments of amino acids that comprise at least about 48%, at least about 48.5%, at least about 49%, at least about 49.5%, or at least about 50%, of the amino acids of the protein composition.

In various embodiments, SDP compositions provided herein can have glycine-alanine (GA) segments of amino acids that comprise at least about 59% of the amino acids of the SDP composition. In some cases, SDP compositions provided herein can also have GA segments of amino acids that comprise at least about 59.5%, at least about 60%, at least about 6.5%, at least about 61%, or at least about 61.5%, of the amino acids of the protein composition.

Protein compositions provided herein can be prepared by a process comprising heating an aqueous fibroin solution at an elevated pressure, wherein the aqueous fibroin solution comprises lithium bromide at a concentration of at least 8M, and wherein the aqueous fibroin solution is heated to at least about 105° C. (221° F.) under a pressure of at least about 10 PSI for at least about 20 minutes; to provide the protein composition, wherein the protein composition comprises less than 8.5% serine amino acid residues. Therefore, methods of preparing a SDP composition are also provided herein. Methods of preparing a SDP composition provided herein can include one or more of the process steps described herein.

In some cases, methods of preparing provided herein can use lithium bromide having a concentration between about 8.0M and about 11M. In some embodiments, the concentration of lithium bromide is about 9M to about 10M, or about 9.5M to about 10M.

In some embodiments, the aqueous fibroin solution that contains lithium bromide is heated to at least about 107° C. (225° F.), at least about 110° C. (230° F.), at least about 113° C. (235° F.), at least about 115° C. (239° F.), or at least about 120° C. (248° F.).

In some embodiments, the aqueous fibroin solution that contains lithium bromide is heated under a pressure of at least about 12 PSI, at least about 14 PSI, at least about 15 PSI, or at least about 16 PSI, up to about 18 PSI, or up to about 20 PSI.

In some embodiments, the aqueous fibroin solution that contains lithium bromide is heated for at least about 20 minutes, at least about 30 minutes, at least about 45 minutes, or at least about 1 hour, up to several (e.g., 12-24) hours.

In some embodiments, the protein composition can be dissolved in water at 40% w/w without observable precipitation.

In some embodiments, the fibroin has been separated from sericin.

In some embodiments, lithium bromide has been removed from the protein composition to provide a purified protein composition. In various embodiments, the protein composition has been isolated and purified, for example, by dialysis, filtration, or a combination thereof.

In additional embodiments, the protein composition has properties as described above, and amino acid compositions as described above regarding serine, glycine, and alanine content.

In various embodiments, the protein composition re-dissolves after drying as a thin film, a property not found with native fibroin. The protein composition can lack beta-sheet protein structure in solution. The protein composition can maintain an optical absorbance in solution of less than 0.25 at 550 nm after at least five seconds of sonication.

In one specific embodiment, the invention provides a protein composition prepared by a process comprising heating an aqueous fibroin solution at an elevated pressure, wherein the aqueous fibroin solution comprises lithium bromide at a concentration of 9-10M, and wherein the aqueous fibroin solution is heated to a temperature in the range of about 115° C. (239° F.) to about 125° C. (257° F.), under a pressure of about 15 PSI to about 20 PSI for at least about 30 minutes; to provide the protein composition, wherein the protein composition comprises less than 6.5% serine amino acid residues. and the protein composition has an aqueous viscosity of less than 10 cP as a 15% w/w solution in water.

SDP compositions are chemically distinct from native silk fibroin protein as a result of the preparation process, resulting in changes in amino acid content and the formation of terminal amide groups. The resulting SDP has enhanced solubility and stability in aqueous solution. The SDP can be used in a method for forming, for example, ophthalmic formulations with a protein composition described herein, for example, an aqueous solution of the protein composition. The solution can include about 0.01% to about 92% w/v SDP. The solution can be about 8% to about 99.9% w/v water.

In some embodiments, processes are provided that induces hydrolysis, amino acid degradation, or a combination thereof, of fibroin protein such that the average molecular weight of the protein is reduced from about 100-200 kDa for silk fibroin produced using prior art methods to about 30-90 kDa, or about 30-50 kDa, for the SDP material described herein. The resulting polypeptides can be a random assortment of peptides of various molecular weights averaging to the ranges recited herein.

In addition, the amino acid chemistry can be altered by reducing cysteine content to non-detectable levels by standard assay procedures. For example, the serine content can be reduced by over 50% from the levels found in the native fibroin, which can result in increases of overall alanine and glycine content by 5% (relative amino acid content), as determined by standard assay procedures. The SDP material can have a serine content of less than about 8% relative amino acid content, or a serine amino acid content of less than about 6% relative amino acid content. The SDP material can have a glycine content above about 46.5%, and/or an alanine content above about 30% or above about 30.5%. The SDP material can have no detectable cysteine content, for example, as determined by HPLC analysis of the hydrolyzed polypeptide of the protein composition. The SDP material can form 90% less, 95% less, or 98% less beta-sheet secondary protein structures as compared to native silk fibroin protein, for example, as determined by the FTIR analysis.

Stability Evaluations. The stability of a protein solution can be evaluated a number of different ways. One suitable evaluation is the Lawrence Stability Test described below in Example 1 below. Another suitable evaluation is the application of sonication to a protein solution, followed by optical absorbance analysis to confirm continued optical clarity (and lack of aggregation, beta-sheet formation, and/or gelation). Standard sonication, or alternatively ultrasonication (sound frequencies greater than 20 kHz), can be used to test the stability of an SDP solution. Solutions of SDP are stable after subjecting to sonication. The SDP composition maintains an optical absorbance at 550 nm of less than 0.25 for at least two hours after five seconds of sonication. For example, a 5% w/w solution of the protein composition can maintain an optical absorbance of less than 0.1 at 550 nm after five seconds of sonication at ~20 kHz, the standard conditions used for the sonication described herein. In various embodiments, SDP composition aqueous solutions do not gel upon sonication at concentrations of up to 10% w/w. In further embodiments, SDP composition aqueous solutions do not gel upon ultrasonication at concentrations of up to 15% w/w, up to 20% w/w, up to 25% w/w, up to 30% w/w, up to 35% w/w, or up to 40% w/w.

Low viscosity. As a result of its preparation process and the resulting changes in the chemical structures of its peptide chains, SDP has a lower viscosity than native silk fibroin (PASF). As a 5% w/w solution in water (at 25.6° C.), native silk fibroin has a viscosity of about 5.8 cP, whereas under the same conditions, SDP has a viscosity of about 1.8 cP, and SDP-4 has a viscosity of about 2.7 cP. SDP maintains a low viscosity compared to PASF at higher concentrations as well. The SDP composition can have an aqueous viscosity of less than 5 cP, or less than 4 cP, as a 10% w/w solution in water. In various embodiments, SDP remains in solution up to a viscosity of at least 9.8 cP. SDP also has an aqueous viscosity of less than 10 cP as a 15% w/w solution in water. SDP can also have an aqueous viscosity of less than 10 cP as a 24% w/w solution in water.

The process described herein provides a protein composition where the fibroin light chain protein is not discernable after processing, as well when the sample is run using standard Sodium Dodecyl Sulfate Polyacrylamide Gel Electrophoresis (SDS-PAGE) electrophoresis methods undertaken with a NuPAGE™ 4%-12% Bis-Tris protein gel (ThermoFisher Scientific, Inc.). For example, in one embodiment, the SDP material can have the fibroin light chain over 50% removed when compared to native silk fibroin protein. Furthermore, the resulting SDP material forms minimal to no beta-sheet protein secondary structure post-processing, while silk fibroin solution produced using prior art methods forms significant amounts of beta-sheet secondary structure. In one embodiment, the SDP material can be prepared by processing silk fibroin fibers under autoclave or autoclave-like conditions (i.e., approximately 120° C. and 14-18 PSI) in the presence of a 40-60% w/v lithium bromide (LiBr) solution.

SDP Composition Fractions

Silk Technologies, Ltd. has developed the silk-derived protein (SDP) product that can be readily incorporated into ophthalmic product formulations for reducing inflammation and enhancing the wound healing process. The SDP product can be separated into smaller protein fractions or sub-populations based on molecular weight to enhance the anti-inflammatory and wound healing properties. SDP protein sub-populations, also referred to as fractions or fragments, can be separated by any suitable and effective method, for example, by size exclusion chromatography or membrane dialysis. For example, the fractions can be separated in to 2-4 different groups based on decreasing average molecular weights. Example 6 describes one method for preparing four different fractions that have the same overall amino acid content and terminal amide content but different average molecular weights. It was surprisingly discovered that the different fractions also possess different biological properties, for example, for reducing inflammation in the body and in various tissues as a result of differences in cellular uptake of the different fractions.

This disclosure therefore provides methods of reducing inflammation and/or enhancing wound healing using SDP, including low average molecular weight fractions of SDP. Also described are compositions for reducing inflammation in the treatment of ocular conditions, such as, but not limited to, dry eye disease, and/or injury, including corneal wounds. The treatments can include the administration of a formulation that includes SDP, or a low molecular weight SDP sub-population. In certain embodiments, the invention provides methods for treating a disease state and/or wound comprising administering to a subject in need thereof a composition comprising low molecular weight SDP (e.g., SDP-3 or SDP-4).

The methods can include applying a composition of SDP fractions to diseased or injured tissue. The protein fractions can have primary amino acid sequences that differ (via summation of absolute value differences) from native fibroin by at least 4% with respect to the combined amino acid content of serine, glycine, and alanine. A plurality of the protein fragments can terminate in amide (—C(=O)NH$_2$) groups. Compositions provided herein may have a serine content that is reduced by greater than 40% compared to native fibroin, wherein the serine content is at least about 5%. The cysteine disulfide bonds between the fibroin heavy and fibroin light protein chains of fibroin may be reduced or eliminated. In some embodiments, at least 75 percent of the protein fragments have a molecular weight of less than about 100 kDa. Such compositions reduce inflammation, and promote cell migration and/or proliferation in the tissue to treat the disease state and/or enhance closure of the wound. The SDP compositions possess enhanced solubility and stability in an aqueous solution.

SDP composition fractions can have an average molecular weight between about 2 kDa and 60 kDa. In one embodiment, a low molecular weight fraction having an average molecular weight of 25-38 kDa, of 32-35 kDa, or about 34 kDa±5%, is isolated, which fraction is referred to herein as SDP-4.

In some embodiments, at least 60 percent of the protein fragments have a molecular weight of less than about 60 kDa, or less than about 55 kDa, to promote cell migration and proliferation in the tissue to close the wound. In another embodiment, at least 90 percent of the protein fragments have a molecular weight of less than about 100 kDa and promote cell migration and proliferation in the tissue to close the wound.

In some embodiments, at least 80 percent of the protein fragments have a molecular weight between about 10 kDa and 85 kDa. In some embodiments, at least 50 percent of the protein fragments have a molecular weight between about 20 kDa and 60 kDa. In some embodiments, at least 85 percent of the protein fragments have a molecular weight of greater than about 10 kDa. In some embodiments, at least 90 percent of the protein fragments have a molecular weight of greater than about 5 kDa.

In certain embodiments, the invention provides an SDP composition comprising low molecular weight SDP and a pharmaceutically acceptable carrier. The low molecular weight SDP can have an average molecular weight of less than 60 kDa. In some embodiments, the low molecular weight SDP is less than 40 kDa and the fraction reduces inflammation and/or enhances cell migration and/or proliferation.

In one embodiment, the low molecular weight SDP, for example, SDP-4, is 10%, 20%, 30%, 40%, 50%, 60%, 70%, 80%, 90% or greater of the total SDP in a composition. In some embodiments, the composition does not comprise high molecular weight SDP, for example, the sample has an average molecular weight of less than about 35 kDa.

In one embodiment, the SDP-4 fraction has an average molecular weight of 33-35 kDa, as determined by SDS-PAGE/ImageJ analysis, as previously described above, and a pH 8.1-8.3, an osmolarity of about 23 mOsm, and a viscosity of about 1.5-3 cP at 25° C., each as a 50 mg/mL solution in water.

Various compositions can be prepared to include low molecular weight protein fragments or high molecular weight protein fragments or combinations thereof. Low molecular weight protein fragments can reduce inflammation and/or enhance cell migration and/or proliferation on a diseased tissue surface and/or wound. Low molecular weight protein fragments are also useful in treating inflamed tissue surfaces due to an active disease state and/or the presence of a wound or wounds. In some cases, it may be useful to apply a composition of low molecular weight protein fragments to enhance the wound healing process. These cases may include wounds acquired on the battlefield during war, surgical wounds of a person who desires faster healing, for example, of an infection or for pain relief. The wound healing process is enhanced by increasing cell numbers, reducing inflammatory molecules, such as MMP-9, and/or increasing epithelial cell proliferation.

High molecular weight protein fragments may increase cell adhesion to the basement membrane or aid in basement membrane formation. In some cases, it may be useful to apply a composition of high molecular weight protein fragments for chronic wounds or wounds that fester or wounds that have difficulty healing up, such as diabetic ulcers or skin burns. Whereas low molecular weight protein fragments may be involved in wound closure rate, high molecular weight protein fragments may be involved in wound closure quality. In some cases, it may be used to apply a composition of carefully selected amounts of low molecular weight protein fragments and high molecular weight protein fragments for optimal wound healing rate and quality. The wound healing process is enhanced by increasing structural proteins, such focal adhesion kinases (FAK) and/or tight junctions between cells, such as zonula occluden (ZO-1) structures.

Low average molecular weight fractions such as SDP-4 possess certain properties making the fraction distinct from SDP and higher molecular weight fractions. For example, SDP cellular uptake is dependent on molecular weight of the peptide chains. SDP peptide molecules smaller than about 60 kDa in size are readily absorbed by cells in culture, and more specifically human corneal limbal epithelial (hCLE) cells. SDP molecules larger than about 60 kDa in size are mostly excluded from being absorbed by the cell cultures. It is also important to note that SDP molecules do not co-localize with lysosomal-associated membrane protein 1 (LAMP-1), which is a marker for the lysosomal endocytotic degradation pathway. As a result, the SDP molecules appear to associate with a non-specified cellular membrane receptor, in which molecules of less than about 60 kDa are then absorbed by the hCLE cells. More importantly, because the SDP molecules are not absorbed through the lysosomal degradation pathway they are bioavailable and able to elicit biological activity.

SDP Formulations

The SDP compositions and sub-fractions described herein can be formulated with water and/or a pharmaceutical carrier. The pharmaceutical carrier can be, for example, phosphate buffered saline, a film, a fiber, a foam, a hydrogel, a protein or polymer matrix, a three-dimensional scaffold, a microparticle, a nanoparticle, a polymer, or a mat. In some embodiments, the protein fragments may be attached to a substrate such as a corneal transplant, a wound dressing, a contact lens, a tissue, a tissue-graft, or a degradable material. In a specific embodiment, the carrier is phosphate buffered saline, for example, in an ocular formulation.

In some embodiments, ophthalmic compositions are provided for the treatment of dry eye syndrome in a human or mammal. Compositions provided herein can be an aqueous solution that includes an amount of SDP effective for treating dry eye syndrome. For example, the effective amount of the SDP in the aqueous solution can be about 0.01% by weight to about 80% by weight SDP. In other embodiments, the aqueous solution can include SDP at about 0.1% by weight to about 10% by weight, or about 0.5% by weight to about 2% by weight. In certain specific embodiments, the ophthalmic composition can include about 0.05% w/v SDP, about 0.1% w/v SDP, about 0.2% w/v SDP, about 0.25% w/v SDP, about 0.5% w/v SDP, about 0.75% w/v SDP, about 1% w/v SDP, about 1.5% w/v SDP, about 2% w/v SDP, about 2.5% w/v SDP, about 5% w/v SDP, about 8% w/v SDP, or about 10% w/v SDP.

In various embodiments, the ophthalmic formulation can include additional components in the aqueous solution, such as a demulcent agent, a buffering agent, and/or a stabilizing agent. The demulcent agent can be, for example, hyaluronic acid (HA), hydroxyethyl cellulose, hydroxypropyl methylcellulose, dextran, gelatin, a polyol, carboxymethyl cellulose (CMC), polyethylene glycol, propylene glycol (PG), hypromellose, glycerin, polysorbate 80, polyvinyl alcohol, or povidone. The demulcent agent can be present, for example, at about 0.01% by weight to about 10% by weight, or at about 0.2% by weight to about 2% by weight. In one specific embodiment, the demulcent agent is HA. In various embodiments, the HA can be present at about 0.2% by weight of the formulation.

The buffering or stabilizing agent of an ophthalmic formulation can be phosphate buffered saline, borate buffered saline, citrate buffer saline, sodium chloride, calcium chloride, magnesium chloride, potassium chloride, sodium bicarbonate, zinc chloride, hydrochloric acid, sodium hydroxide, edetate disodium, or a combination thereof.

An ophthalmic formulation can further include an effective amount of an antimicrobial preservative. The antimicrobial preservative can be, for example, sodium perborate, polyquaterium-1 (e.g., Polyquad® preservative), benzalkonium (BAK) chloride, sodium chlorite, brimonidine, brimonidine purite, polexitonium, or a combination thereof.

An ophthalmic formulation can also include an effective amount of a vasoconstrictor, an anti-histamine, or a combination thereof. The vasoconstrictor or antihistamine can be naphazoline hydrochloride, ephedrine hydrochloride, phenylephrine hydrochloride, tetrahydrozoline hydrochloride, pheniramine maleate, or a combination thereof.

In one embodiment, an ophthalmic formulation can include an effective amount of SDP as described herein in combination with water and one or more ophthalmic components. The ophthalmic components can be, for example, a) polyvinyl alcohol; b) PEG and hyaluronic acid; c) PEG and propylene glycol, d) CMC and glycerin; e) propylene glycol and glycerin; f) glycerin, hypromellose, and PEG; or a combination of any one or more of the preceding components. The ophthalmic formulation can include one or more inactive ingredients such as HP-guar, borate, calcium chloride, magnesium chloride, potassium chloride, zinc chloride, and the like. The ophthalmic formulation can also include one or more ophthalmic preservatives such as sodium chlorite (Purite® preservative ($NaClO_2$), polyquad, BAK, EDTA, sorbic acid, benzyl alcohol, and the like. Ophthalmic components, inactive ingredients, and preservatives can be included at about 0.1% to about 5% w/v, such as about 0.25%, 0.3%, 0.4%, 0.5%, 1%, 2%, 2.5%, or 5%, or a range in between any two of the aforementioned values.

Ophthalmic formulations for the treatment of ophthalmic disorders in a human or mammal can be prepared, wherein the ophthalmic formulation comprises water and an effective amount of the SDP as described above. The ophthalmic composition can be used as an eye treatment in a human or mammal, where the ophthalmic composition comprises water, one or more of a buffering agent and stabilizing agent, and an effective amount of the SDP or a sub-fraction thereof.

The SDP is highly stable in water, where shelf life solution stability is more than twice that of native silk fibroin in solution. For example, the SDP is highly stable in water, where shelf life solution stability is more than 10 times greater compared to native silk fibroin in solution. The SDP material, when in an aqueous solution, does not gel upon sonication of the solution at a 5% (50 mg/mL) concentration. In other embodiments, the SDP material, when in an aqueous solution, does not gel upon sonication of the solution at a 10% (100 mg/mL) concentration.

Therapeutic Methods

The invention provides for the use of SDP in formulations to reduce inflammation, for example, inflammation on or in the human cornea. Such reduction in inflammation has been demonstrated in both in vitro and in vivo experimental models. Specifically, work was undertaken to show that SDP works to reduce inflammation in human corneal models by inhibiting NF-κB-associated cell signaling pathways (see FIGS. 1 and 2), which is a known driver of inflammation in the body, in which one specific example is dry eye disease. It was found that inhibition of these pathways ultimately led to reduced genetic expression and tissue residence of MMP-9, which is a known driver of dry eye and ocular inflammation (see FIG. 4). Although the studies listed here are specific to corneal inflammation, the biological processes affected are also present throughout the various tissues of the body. As a result, the work disclosed herein regarding the cornea can be extended to other tissue systems containing an epithelial surface, in which one such example is skin.

The invention thus provides methods for reducing inflammation and for treating wounds, including corneal wounds, comprising the administration of SDP to the site of interest. The methods can include administering a formulation comprising a composition of silk-derived protein (SDP), or molecular fractions thereof, to inflamed tissue, e.g., living animal tissue in a wound. In some embodiments, the subject has an ocular condition that results in inflamed tissue, for example, as in dry eye disease. In some embodiments, the wound is an ocular wound, a surgical wound, an incision, or an abrasion. The ocular wound can be, for example, a corneal wound SDP can thus be used to treat and/or reduce the inflammation caused by conditions such as a wound, infection, or disease. Examples of such conditions include ocular wounds, surgical wounds, incisions, or abrasions. In some cases, the inflammation is caused by an ocular condition, such as, dry eye disease or syndrome, corneal ulcer, corneal erosion, corneal abrasion, corneal degeneration, corneal perforation, corneal scarring, an epithelial defect, keratoconjunctivitis, idiopathic uveitis, corneal transplantation, age-related macular degeneration (AMD, wet or dry), diabetic eye conditions, blepharitis, glaucoma, ocular hypertension, post-operative eye pain and inflammation, posterior segment neovascularization (PSNV), proliferative vitreoretinopathy (PVR), cytomegalovirus retinitis (CMV), endophthalmitis, choroidal neovascular membranes (CNVM), vascular occlusive diseases, allergic eye disease, tumors, retinitis pigmen-tosa, eye infections, scleritis, ptosis, miosis, eye pain, mydriasis, neuralgia, cicatrizing ocular surface diseases, ocular infections, inflammatory ocular diseases, ocular surface diseases, corneal diseases, retinal diseases, ocular manifestations of systemic diseases, hereditary eye conditions, ocular tumors, increased intraocular pressure, herpetic infections, ptyrigium (scleral tumor), wounds sustained to ocular surface, post-photorefractive keratotomy eye pain and inflammation, thermal or chemical burns to the cornea, scleral wounds, keratoconus and conjunctival wounds. In some embodiments, the inflammation and/or ocular condition is caused by aging, an autoimmune condition, trauma, infection, a degenerative disorder, endothelial dystrophies, and/or surgery. In one specific example, SDP is used in a formulation to treat dry eye syndrome.

Thus, in various embodiments, SDP and/or fractions thereof such as SDP-4, can be used to inhibit mediators of redox-regulated activation of the canonical NF-κB pathway through scavenging of reactive oxygen species (ROS), for example hydrogen peroxide, within the cells of the ocular environment to reduce the inflammation that causes dry eye syndrome. Evidence of reduced dry eye symptoms can be a reduction in MMP-9 and TNF-α gene transcription, which are driven by the activation of the NF-κB signaling pathway. Furthermore, MMP-9 enzyme presence in the cornea tissue will also be reduced.

The following Examples are intended to illustrate the above inventions and should not be construed as to narrow its scope. One skilled in the art will readily recognize that the Examples suggest many other ways in which the inventions could be practiced. It should be understood that numerous variations and modifications may be made while remaining within the scope of the inventions.

EXAMPLES

Example 1. SDP Preparation and the Lawrence Stability Test

Materials.

Silkworm cocoons were obtained from Tajima Shoji Co., Ltd., Japan. Lithium bromide (LiBr) was obtained from FMC Lithium, Inc., NC. An autoclave was obtained from Tuttnauer Ltd., NY. The 3.5 kDa molecular-weight cutoff (MWCO) dialysis membranes were obtained from Thermo-Scientific, Inc., MA. An Oakton Bromide (Br⁻) double-junction ion-selective electrode was obtained from ISE, Oakton Instruments, IL.

Processing.

Two samples, SDP and PASF, were prepared. Briefly, SDP was produced by submerging pupae-free, cut silkworm cocoons (3-5 cuts/cocoon) into 95° C. heated, deionized water (diH$_2$O) containing 0.3 wt % NaCO$_3$ at 233 mL water/gram of cocoons. Cocoons were agitated in this solution for 75 minutes to dissolve sericin, thereby releasing it from the silk fibers. The fibers were subsequently washed four times in like dilutions of diH$_2$O for 20 minutes per rinse to remove residual sericin. The fibers were then dried in a convection oven at 60° C. for 2 hours, weighed, and dissolved in 54 wt % LiBr in water at a ratio of 4× LiBr volume per gram of extracted fiber. This solution was covered and then warmed in a convection oven at 60° C. for 2 hours to expedite extracted fiber dissolution. The solution was then placed in an autoclave and exposed to sterilization conditions (121° C., 17 PSI, 97-100% humidity) for 30 minutes to facilitate fibroin transformation. The resulting fibroin solution was allowed to cool to room temperature, then diluted to 5% with diH$_2$O and dialyzed to remove LiBr salts using a 3,500 Da MWCO membrane. Multiple exchanges were performed in diH$_2$O until Br⁻ ions were less than 1-ppm as determined in the hydrolyzed fibroin solution read on an Oakton Bromide (Br⁻) double-junction ion-selective electrode. The solution was then further filtered using a 1-5 µm porosity filter followed by filtration through a 0.2 µm polishing filter.

A 'control' silk fibroin solution was prepared to provide the 'PASF Solution'. Except the autoclave step, the same process was performed as described above. A sampling volume (5 mL) from each sample was placed in separate 20 mL glass beakers and the beakers were sealed with foil. The samples were then subjected to the Lawrence Stability Test.

The Lawrence Stability Test is performed by placing the aqueous protein test solution (5% w/v, 50 mg/mL) within the autoclave chamber. The autoclave is then activated for a cycle at 121° C., 17 PSI, for 30 minutes, at 97-100% humidity. After completion of the cycle, the solution is allowed to cool and is then removed from the autoclave chamber. The solution is then shaken to observe solution gelation behavior. If the solution has gelled upon shaking for ~10 seconds, the sample fails the Lawrence Stability Test. Failing the test indicates that the material is inherently unstable as a protein solution.

The Lawrence Stability Test was performed on both the SDP solution and the PASF solution. The PASF solution sample gelled immediately and therefore failed the Lawrence Stability Test. Conversely, the SDP solution sample remained in solution indefinitely and therefore passed the Lawrence Stability Test. The lack of gelation can be attributed to the fact that the SDP solution production incorporates the autoclave-processing step under the conditions described above.

Example 2. SDP Molecular Weight Characterization

To evaluate the effect of processing on the molecular weight distribution of solubilized protein, SDP Solution and PASF Solution were subjected to polyacrylamide gel electrophoresis (PAGE), which separates proteins by molecular weight. Specifically, 15 µg of each sample was mixed with running buffer containing sodium dodecyl sulfate and dithiothreitol (Biorad Inc., CA) to remove any secondary folding structures and disulfide bonds, respectively. The mixtures were then heated to 70° C. for 5 minutes. The mixtures were loaded along with a 2.5-200 kDa molecular weight ladder (Life Technologies, CA) onto pre-cast, 4-12% polyacrylamide gradient gels containing Bis-Tris buffer salts (Life Technologies, CA), and then exposed to 120V electric field for 90 minutes on a BioRad PowerPac Power supply (BioRad Inc., CA). The gels were then removed and placed in Coomassie Blue stain for 12 hours to stain proteins, followed by 6 hours of washing in diH$_2$O. The gels were then scanned on a Biorad GS-800 Calibrated Desitometer (BioRad Inc., CA).

The results show that the processing employed to prepare the SDP solution significantly shifts the weight average molecular weight from 97 kDa for native fibroin (PASF) to about 53 kDa for SDP. The shift in molecular weight clearly indicates a transformation of the primary and secondary structure of the original native fibroin and break-up of the peptide chains via terminal amide-forming cleavages. In addition, the fibroin light chain of fibroin is not present in the SDP after the autoclaving process (visible at 23-26 kDa in Lane 2 for the prior art fibroin), which indicates that the fibroin light chain portion of the protein has been degraded or removed by the processing. These results demonstrate that the autoclave processing transforms the native fibroin protein to a new material that has smaller peptide fragments than the native fibroin protein. The process further degrades/modifies the fibroin light chain. These transformations result in an SDP material that possesses enhanced solution stability as a result of these chemical changes.

Further analysis of SDP shows that the average molecular weight of the composition is about 53 kDa. Furthermore, about 77% of the peptide chains of SDP are within the range of 10-100 kDa, about 73% of the peptide chains of SDP are within the range of 10-85 kDa, about 66% of the peptide chains of SDP are within the range of 15-85 kDa, about 49% of the peptide chains of SDP are within the range of 20-60 kDa, and about 31% of the peptide chains of SDP are within the range of 25-50 kDa.

Example 3. SDP Stability Study

To further determine the functional impact of the autoclave process on the stability of the resulting SDP compared to the stability of prior art fibroin, the samples were analyzed using the methods of Wang et al. (*Biomaterials* 2008, 29(8): 1054-1064) to mimic a well-characterized model of silk fibroin protein gelation. Volumes of both samples (0.5 mL, SDP and PASF) were added to 1.7 mL clear centrifuge tubes and subjected to sonication (20 kHz, 15 seconds). The clear tubes containing the solutions were then visually monitored for gel formation as a screen for gelation.

The SDP Solution samples failed to form gels, demonstrating enhanced stability. Even 3-months post-sonication, the SDP samples remained in solution and lacked protein aggregation as determined by visual inspection. The PASF Solution sample gelled rapidly (within 2 hours) following sonication. These results further indicate that the autoclave process transforms native isolated fibroin into a new material and induces stability to the resulting SDP material.

Example 4. In Vitro Analysis of NF-κB Cell Signaling Pathway in Human Corneal Limbal Epithelium (hCLE) Cultures The p65 assay as described by Lan et al. (*Nuclear Factor-κ B: Central Regulator in Ocular Surface Inflammation and Diseases*, The Ocular Surface, 10, 137-148 (2012)) was utilized to assess the potential anti-inflammatory activity of SDP on hCLE cell cultures. As described earlier, the nuclear transcription factor p65 is part of the NF-kB complex, which translocates into the cell nucleus upon activation to facilitate proinflammatory gene expression, including TNF-α and MMP-9. To assess p65 activity in vitro, confluent hCLE cultures were treated with either PBS or PBS containing the potent inflammatory cytokine TNF-α, an autocrine mediator of the NF-κB pathway. Cells were then treated with PBS or PBS containing 0.1% or 1.0% SDP, respectively. Staining of p65 was localized primarily to the cytoplasm for untreated controls, which is expected for cells in a non-inflammatory state (FIG. 1A). However, p65 staining was confined to the nucleus for cells challenged with TNF-α in the culture medium, indicating that activation of NF-κB inflammatory pathway had taken place (FIG. 1B). Interestingly, p65 staining for SDP-treated cells was largely confined to the cytoplasm and demonstrated a dose-dependent sequestration whereby less nuclear localization was exhibited with cells dosed with higher SDP concentrations (FIG. 1C-D). These results indicate that the SDP protein inhibits the NF-κB inflammatory response in human corneal epithelium in vitro.

The inhibition of the NF-κB inflammatory signaling pathway by SDP was further investigated through characterizing TNF-α and MMP-9 gene expression, which are known to be upregulated during NF-κB-driven inflammation processes. More specifically, increased gene expression of TNF-α and MMP-9 is mediated by activation of NF-κB, and are biomarkers for inflammatory cell signaling pathways. Gene expression was measured using qPCR on hCLE cultures that were pre-incubated with both PBS and TNF-α cytokine, and then subsequently treated with and without 0.5% wt./vol. SDP as above described. It was observed that the addition of SDP caused no change in basal gene expression of TNF-α and MMP-9 (FIG. 2). However, stimulation with TNF-α evoked a significant rise in expression of both genes (FIG. 2), which replicates the human NF-κB driven inflammation cascade. Importantly, treatment with SDP at the time of TNF-α stimulation evoked a ~6-fold reduction in expression of both TNF-α and MMP-9, thereby demonstrating a potent anti-inflammatory effect of SDP on TNF-α-mediated NF-κB gene expression. These results corroborate with the previous p65 assay results, collectively supporting that SDP inhibits NF-κB activation, and as a result inhibits proinflammatory gene expressing (viz., TNF-α and MMP-9).

Next, studies were carried out in a rabbit corneal epithelial injury model to evaluate whether the anti-inflammatory effects of SDP could be extended in vivo. Rabbits were subjected to surgical denudement of the corneal epithelium to instigate acute inflammatory cascades, and then treated with eye drops of PBS, PBS plus 0.5%, or PBS plus 2% SDP over 72-hours with 6-hour dosing frequency at approximately 50 µL droplet volume until complete epithelial healing had occurred. Explanted tissue was then cryosectioned and immunostained with antibodies against MMP-9 protein. The native, non-wounded rabbit cornea exhibited minimal MMP-9 expression as anticipated (FIG. 3A), given that reduced presence of staining indicates minimal inflammation is taking place as described by Kaufmann (*The Practical Detection of MMP-9 Diagnoses Ocular Surface Disease and May Help Prevent Its Complications*, Cornea, 32(2), p 211-216 (2013)). However, corneal denudement followed by PBS treatment showed robust MMP-9 expression throughout the entire epithelial layer, and indicated a high degree of inflammation had occurred (FIG. 3B).

Interestingly, a dose-dependent reduction in rabbit corneal MMP-9 expression was observed with the use of eye drops containing SDP (FIGS. 3C and 3D). Specifically, MMP-9 immunostaining was significantly reduced up to 4-fold for corneas treated with 2% SDP (FIG. 3E). Importantly, attenuated MMP-9 expression did not compromise the integrity of the protective corneal epithelial layer, evidenced by a robust stratified corneal epithelium with SDP treatment. These data indicate the impact that SDP treatment has to reduce inflammation within the corneal epithelial tissue post-injury, evidenced by the reduction in MMP-9 with increasing SDP concentration. Furthermore, these results demonstrate the effective anti-inflammatory capacity of SDP within a living animal tissue environment, and corroborate previous in vitro studies.

Figure 3:
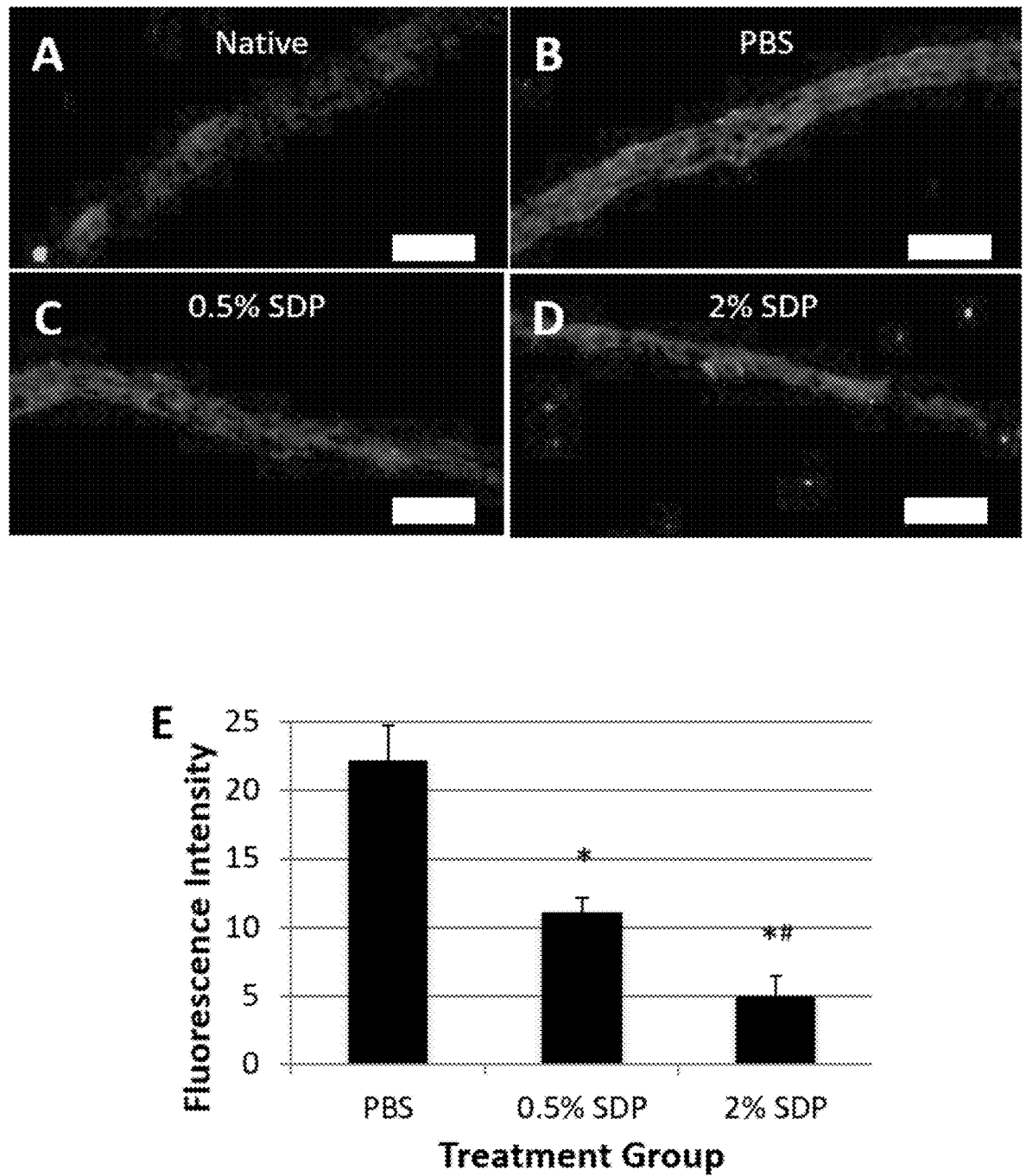
FIG. 3A-E. (A) Representative cross-section image of corneal tissue obtained from native rabbits immunostained for MMP-9. (B-D) Representative immunohistochemical images of corneal cross-sections obtained from rabbits harvested 72-hours post-surgery for the various treatment groups. MMP-9 staining decreased for both SDP treated groups (C and D) when compared to PBS-treated animals (B). (Scale bar=50 µm). (E) Summary graph of measured staining intensity (fluorescence intensity) of MMP-9 in corneas treated with PBS, 0.5% SDP, or 2% SDP (*$p<0.01$ vs. Control; #$p<0.01$ compared to 0.5% SDP, n=3).
Figure 4:
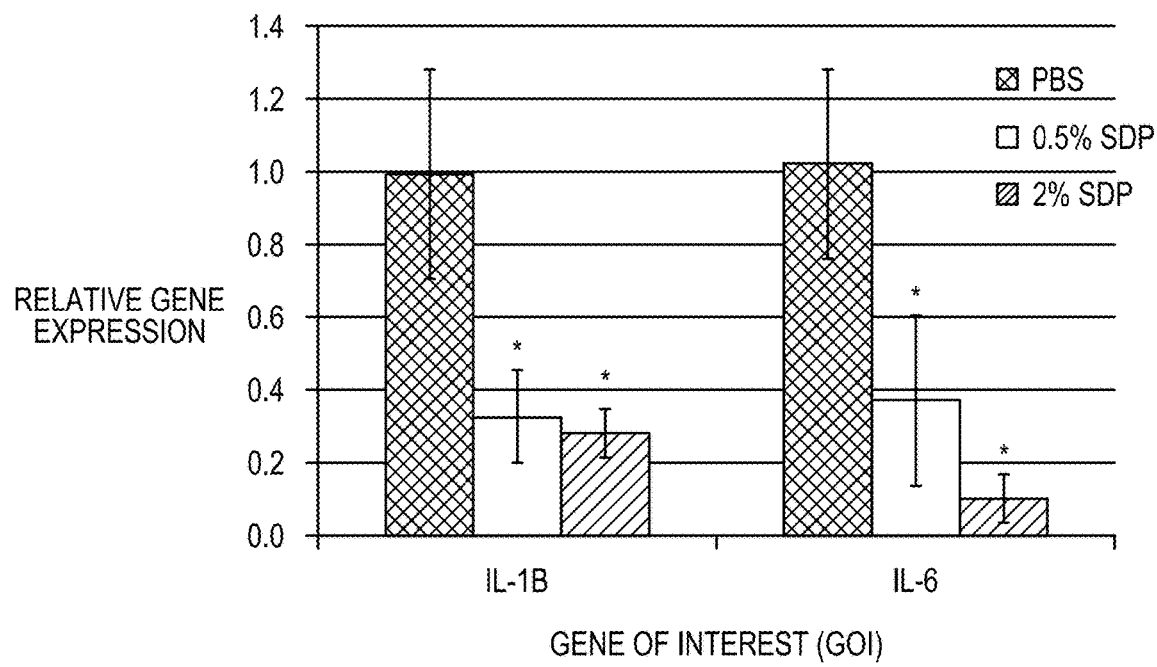
FIG. 4. qPCR results of relative fold gene expression of IL-1β and IL-6 for rabbit corneas treated with PBS, PBS plus 0.5% SDP, and PBS plus 2% SDP over a 72-hour period following surgical denudement of the epithelial surface. IL-1β and IL-6 are known genetic markers of inflammation within the corneal tissue environment. Expression of both markers was significantly reduced in the presence of SDP treatment (*$p<0.01$ vs. PBS for each GOI; n=6).
Figure 5:
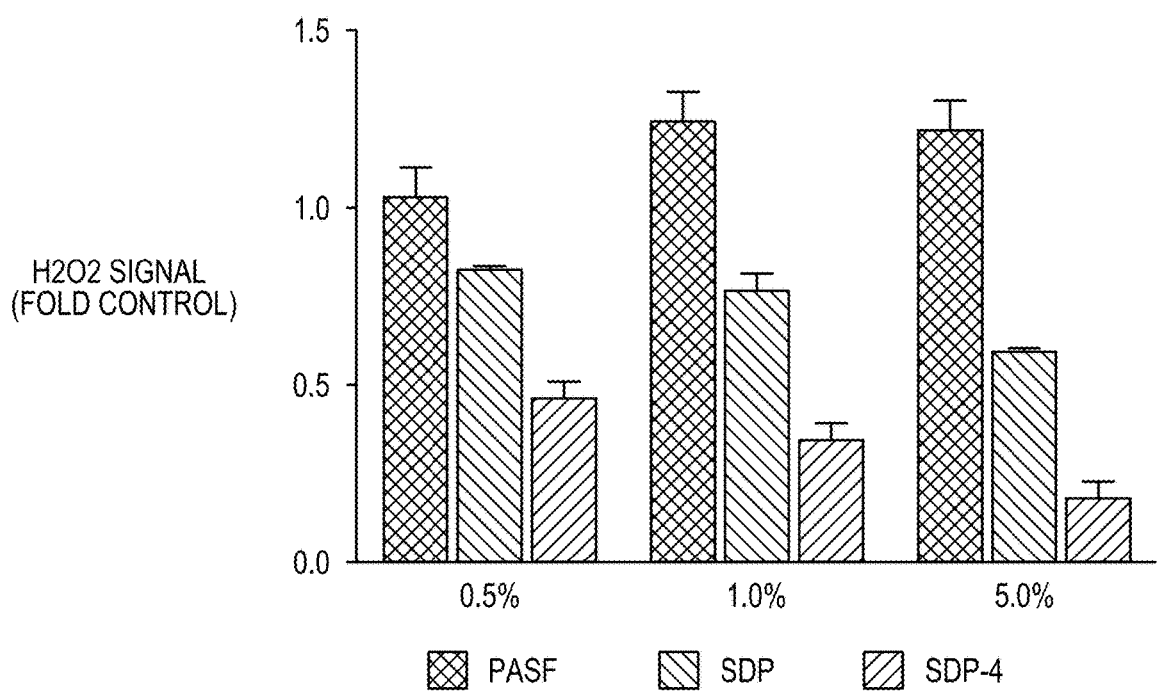
FIG. 5. Summary graph of $H_2O_2$ levels measured by electron paramagnetic resonance (EPR) spectroscopy in the presence of defined concentrations of dissolved proteins (PASF, SDP or SDP-4). $H_2O_2$ (20 µM) was incubated in the absence (Control) or presence of PASF, SDP, or SDP-4 (each at 0.5%, 1%, or 5%), and then introduced to a $H_2O_2$-specific spin probe. EPR signal generated by the oxidized spin probe for each sample was measured and normalized to control samples (i.e., lacking protein). PASF increased EPR signal amplitude with increasing protein concentration. In contrast, SDP evoked a concentration-dependent reduction in EPR signal amplitude, demonstrating that SDP proteins scavenge $H_2O_2$. $H_2O_2$ scavenging was even more robust in the presence of SDP-4 proteins. Error bars are represented as S.D., N=3.

To further bolster the in vivo anti-inflammatory effects of SDP, qPCR was performed on reverse transcribed, total RNA extracted from the rabbit corneal epithelium 72-hours post injury. Specifically, two key biomarkers of inflammatory signaling, cytokines interleukin (IL)-1β and IL-6, were assessed. Expression of both IL-1β and IL-6 was reduced significantly in the presence of SDP treatment (FIG. 4). There was a respective 75% and 95% reduction in gene expression for both SDP concentrations when compared to PBS-treated control animals. These findings demonstrate the capacity of SDP to inhibit inflammatory gene expression in vivo, and further substantiate the above in vivo and in vitro data. Taken together, experimental evidence shows that SDP inhibits inflammatory processes in vivo, which appears to be directly related to the inhibition of NF-κB inflammatory signaling pathway activation by the presence of SDP.

Materials and Methods.

Sdp Production.

*Bombyx mori* silkworm cocoons were purchased from Tajima Shoji Co. (Yokohama, Japan). The silk solution was prepared from a batch of 5 g of cocoons that were cut into three pieces each. The cocoons were boiled in 2 L of 0.03M $Na_2CO_3$ (Sigma-Aldrich) for 45 minutes to remove the sericin protein. After four rinses in deionized water the extracted silk fibroin fibers were dried at room temperature overnight. The dried silk fibroin fibers were then dissolved in a concentrated solution of 9.7 M LiBr solution (Sigma-Aldrich) for 2 hours at 60° C. Then, the solution was autoclaved at and 121 OC under 15 PSI for 30 minutes to execute the SDP chemical transformation. The autoclaved SDP solution was then dialyzed against an approximately 200× volume of water using Snake-Skin dialysis tubing (Thermo Fisher Scientific, Inc.) with a 3,500 molecular weight cut-off (MWCO) for 48-hours and six water exchanges at 1, 4, 8, 12, 12, and 12 hour intervals. The dialyzed solution was next centrifuged twice at 10,000×g for 20 minutes to remove impurities by decanting the supernatant each time. Protein concentration was then calculated by measuring the weight loss on drying of 1 mL samples of SDP solution (n=3). The solution was finally diluted to a 5 wt./vol. % (50 mg/mL) concentration using sterile water and stored at 4° C. until use.

Human Corneal Epithelial Cell Culture.

Human corneal limbal epithelial (hCLE) cells were thawed from storage in liquid nitrogen and cultured for 72 hours in keratinocyte-SFM medium (K-SFM, Thermo Fisher Scientific, Inc.) supplemented with 0.2 ng/mL mouse epithelial growth factor (EGF, Thermo Fisher Scientific, Inc.), bovine pituitary extract (BPE, Thermo Fisher Scientific, Inc.), 1% penicillin-streptomycin (P/S, VWR, Inc.) and 0.1% $CaCl_2.2H_2O$ (Thermo Fisher Scientific, Inc.). Standard cell culture conditions (37° C., 5% $CO_2$, >95% humidity) were used during routine passages.

hCLEp65 Staining for NF-κB Activation and Fluorescence Microscopy Analysis.

hCLE cells were grown to ~80% confluency with a 25,000-cells per well seeding density. hCLEs were cultured with DMEM/F12 Media in a glass bottom 24-well plate. Human recombinant TNF-α (PeproTech, London, UK) was supplemented at 10 ng/mL and 100 ng/mL for stimulated cultures over a 12-hour challenge. SDP was added to selected cultures at 1 mg/mL and 10 mg/mL concentration. At the completion of the experiments cultures were fixed using freshly made 4% paraformaldehyde in phosphate buffered saline (PBS). Human p65 antibody (Anti-NF-κB p65, ab16502, Abcam, Cambridge, UK) was added at 1:200 dilution in 1% BSA and 0.1% Tween in PBS and incubated overnight at 4° C. A secondary antibody reactive to anti-rabbit (Alexa Fluor 546, Thermo Fisher Scientific, Inc.) was added at a 1:500 dilution in PBS. In addition, DAPI nuclear stain (Thermo Fisher Scientific, Inc.) was added at a 1:10, 000 dilution in PBS.

Fluorescent images were taken using a 63× objective utilizing a 1.6 Optivar optic. Z-stack images (10-25 layer range) were captured at 0.25 μm slices using a Texas Red filter channel. Image deconvolution was performed on each z-stack using 3D Huygens Deconvolution Software (Scientific Volume Imaging BV, The Netherlands) to assist with reducing background fluorescence. A total of 40 iterations were performed employing the software's classic maximum likelihood estimation algorithm for each z-stack, as it was found that increasing the number of iterations had a minimal effect on improving image quality. All other settings were left at the manufacturer's default settings. Images were produced using maximum intensity projection (MIP) algorithm included in the software, where MIP threshold levels were first determined by default manufacturer's settings for control corneal tissue to establish a relative fluorescent intensity threshold for each channel.

TNF-α Stimulated Inflammation Assay and Gene Expression Analysis by Quantitative Polymerase Chain Reaction (qPCR).

hCLE cells were seeded in 35 mm dishes and grown to ~80% confluency before they were dosed with either PBS or PBS plus 1 ng/mL of recombinant human TNF-α. The cultures were then incubated at 37° C. for 6 hours. The media was then aspirated and the cells were washed with warm 1×PBS before they were treated for 6 hours with concentration-matched SDP fractions at a 5 mg/mL concentration, while control groups were dosed with like volumes of PBS. After the defined time had elapsed, total RNA was harvested from the cells using Qiagen RNeasy Plus Mini Kit (Qiagen, Valencia, Calif., USA), and RNA integrity and quantity were verified using electrophoresis and flow cytometry (2100 Bioanalyzer, Agilent Technologies, Santa Clara, Calif.), and UV absorption (Nanodrop Spectrophotometer, Thermo Scientific). Afterwards, 450 ng of total RNA from each sample was reverse transcribed into cDNA using the High Capacity cDNA Reverse Transcription kit (Applied Biosystems, Life Technologies, Grand Island, N.Y.).

Quantitative PCR (qPCR) was carried out in a StepOne Plus real time PCR system (Applied Biosystems, Life Technologies, Grand Island, N.Y.) using the SYBR Select Master Mix kit (Applied Biosystems, Life Technologies, Grand Island, N.Y.). Genetic expression was performed on total RNA harvested from cells that were not stimulated with TNF-α, as a negative control for the inflammatory stimulus (Native). The expression of candidate genes was normalized against the endogenous control gene β-actin. Relative quantitation was performed using the $2^{(-\Delta\Delta ct)}$ method, where 3 experiments were run for each condition each containing three biological triplicates per condition (N=3, n=3). The population mean was obtained by averaging the means from each experiment, and a pooled standard deviation was calculated for each group. Statistical comparison was performed between groups using dCt values by first performing a one-way ANOVA followed by post-hoc t-tests to determine p-values using Excel Software (Ver. 14.6.7, Microsoft, Inc.) and StatPlus:mac LE software (Ver. 6.1.5.1, AnalystSoft, Inc., Walnut, Calif.). The following specific primer sets were used for β-Actin, TNF-α and MMP-9 (received from Integrated DNA Technologies, Inc., Coralville, Iowa):

| | (SEQ ID NO: 2) |
|---|---|
| hβ-Actin-Forward: | 5'-AATGTGGCCGAGGACTTTGATTGC-3' |

| | (SEQ ID NO: 3) |
|---|---|
| hβActin-Reverse: | 5'-AGGATGGCAAGGGACTTCCTGTAA-3' |

| | (SEQ ID NO: 4) |
|---|---|
| hTNF-α-Forward: | 5'-GAGGCCAAGCCCTGGTATG-3' |

| | (SEQ ID NO: 5) |
|---|---|
| hTNF-α-Reverse: | 5'-CGGGCCGATTGATCTCAGC-3' |

| | (SEQ ID NO: 6) |
|---|---|
| hMMP-9-Forward: | 5'-TGTACCGCTATGGTTACACTCG-3' |

| | (SEQ ID NO: 7) |
|---|---|
| hMMP-9-Reverse: | 5'GGCAGGGACAGTTGCTTCT-3' |

Rabbit Corneal Injury Model, Immunohistochemical Fluorescent Imaging Analysis, and qPCR Gene Transcription Analysis.

All animals were handled according to the ARVO Statement for the Use of Animals in Ophthalmic and Visual Research, under protocols approved by Institutional Animal Care and Use Committee. Twelve 8-10 week old New Zealand white rabbits were used to evaluate the capability of SDP to reduce MMP-9 production in vivo. Rabbits were anesthetized with intramuscular injections of 35-50 mg/kg ketamine, 5-7.5 mg/kg xylazine, and 0.75 mg/kg acepromazine. Topical proparacaine 0.5 wt./vol. % eye drops were also used as supplemental anesthesia. A #15 Bard-Parker blade was then used to remove 7 mm of the central corneal epithelium to create a void in the epithelial surface.

Subsequently, the rabbits were divided into three treatment groups, where the wounded corneal surface was treated with either 200 μL of sterile phosphate buffered saline (PBS, pH 7.4, vehicle treatment), 5 mg/mL (i.e., 0.5%) or 20 mg/mL (i.e., 2%) SDP solution in PBS. The treatments were administered topically to the wounded eyes, along with topical moxifloxacin antibiotic drops (Vigamox, Alcon, Inc.), immediately following surgery and subsequently at 6-hour intervals until complete epithelial closure had occurred. Throughout the healing process, rabbits were closely monitored for evidence of distress or infection, and epithelial wound closure was examined every 6 hours by applying 50 μL of topical fluorescein solution (Sigma-Aldrich) to the injured cornea and imaging the wound using slit lamp photography under cobalt blue illumination.

Animals from each treatment group were sacrificed immediately after wound healing was completed (72 hours post-surgery), using an overdose of pentobarbital (150 mg/kg) administered into the ear vein, and the corneas from each treatment group were enucleated and excised. For the first three rabbits, the healed epithelial surface was removed and the total RNA was extracted using the Trizol-chloroform method (ThermoFisher Scientific, Inc.). Total RNA from each sample was reverse transcribed into cDNA using the High Capacity cDNA Reverse Transcription kit (Applied Biosystems, Life Technologies, Grand Island, N.Y.). The cDNA was then frozen at −80° C. until use.

The remaining three rabbits had extracted corneas fixed immediately in 2 wt./vol. % paraformaldehyde for 40 minutes (Electron Microscopy Sciences, Hatfield, Pa.). Corneas from the contralateral eyes that did not undergo surgical denudement were also harvested and fixed, to serve as negative controls for the wound healing process. The fixed corneas were subsequently washed three times in PBS for 5 minutes each, and then placed in 30 wt./vol. % sucrose overnight at 4° C. before embedding in Tissue-TEK O.C.T (Sakura Finetek USA Inc., Torrance, Calif., USA) and frozen at −80° C. for cryo-sectioning. Ten-micron thick cross-sections, through the center of the cornea, were obtained and mounted on Superfrost-plus glass slides (Thermo Fisher Scientific, Inc.) for immunohistochemical staining and analysis. Samples were washed three times in PBS and then incubated in blocking buffer containing 1 wt./vol. % BSA (Sigma-Aldrich), 0.25 wt./vol. % Triton-X-100 (Sigma-Aldrich), and 2.5 wt./vol. % goat serum in 1×PBS, for 1 hour at room temperature. After blocking, samples were incubated with murine primary antibody solutions (1:100) for MMP-9 (ab58803, Abcam PLC, Cambridge, UK) overnight at 4° C.

Subsequently, the samples were rinsed thoroughly with PBS and then incubated with Alexa Fluor 488 Green goat anti-mouse secondary antibody (ab150113, Abcam PLC, Cambridge, UK) at a 1:500 dilution for 1 hour at room temperature, protected from light. Samples were also stained with Alexa Fluor® 568 phalloidin (Thermo Fisher Scientific, Inc.) at a 1:200 dilution for 20 minutes at room temperature and protected from light to stain for actin cytoskeletal structure. After washing with PBS, Samples were mounted with VECTASHIELD Mounting Medium with DAPI (Vector Laboratories, Burlingame, Calif., USA) to stain for cell nuclei, and covered with a glass coverslip before imaging.

Fluorescent images were taken using a 63× objective utilizing a 1.6 Optivar optic. Z-stack images (10-25 layer range) were captured at 0.25 m slices using the green fluorescent protein (GFP) filter channel. Image deconvolution was performed on each z-stack using 3D Huygens Deconvolution Software (Scientific Volume Imaging BV, The Netherlands) to assist with reducing background fluorescence. A total of 40 iterations were performed employing the software's classic maximum likelihood estimation algorithm for each z-stack, as it was found that increasing the number of iterations had a minimal effect on improving image quality. All other settings were left at the manufacturer's default settings. Images were produced using maximum intensity projection (MIP) algorithm included in the software, where MIP threshold levels were first determined by default manufacturer's settings for control corneal tissue to establish a relative fluorescent intensity threshold for each channel. Then, native and SDP-treated cornea groups were imaged using these same threshold settings to allow for group comparisons (N=3, n=3) of fluorescent image intensities.

Next, fluorescence intensity of each image was measured using ImageJ software (NIH, Ver. 1.48, NIH) by subtracting the mean integrated color densities of a non-fluorescing region from the traced fluorescent region to eliminate background. Fluorescent intensity values among the different groups were then calculated. Groups were then statistically compared through one-way ANOVA analysis followed by ad hoc t-tests to determine p-values using Excel Software (Microsoft, Inc., Ver. 14.6.7) and StatPlus:mac LE software (AnalystSoft, Inc., Ver. 6.1.5.1).

Quantitative PCR (qPCR) was carried out on an ABI 7000 real time PCR system (Applied Biosystems, Life Technologies) using the SYBR Select Master Mix kit (Applied Biosystems, Life Technologies). Genetic expression was performed on produced cDNA from the harvested from the rabbit corneal epithelium. The expression of candidate genes was normalized against the endogenous control gene β-actin. Relative quantitation was performed using the $2^{(-\Delta\Delta Ct)}$ method. Statistical comparison was performed between groups using dCt values by first performing a one-way ANOVA followed by post-hoc t-tests to determine p-values using Excel Software (Microsoft, Inc., Ver. 14.6.7) and StatPlus:mac LE software (AnalystSoft, Inc., Ver. 6.1.5.1). The following specific primer sets were used for β-Actin, IL-1β and IL-6 genes (received from Integrated DNA Technologies, Inc., Coralville, Iowa):

| | | |
|---|---|---|
| rβ-actin-Forward: | 5'-GCTATTTGGCGCTGGACTT-3' | (SEQ ID NO: 8) |
| rβ-actin-Reverse: | 5'-GCGGCTCGTAGCTCTTCTC-3' | (SEQ ID NO: 9) |
| rIL-1β-Forward: | 5'-TTGAAGAAGAACCCGTCCTCTG-3' | (SEQ ID NO: 10) |
| rIL-1β-Reverse: | 5'-CTCATACGTGCCAGACAACACC-3' | (SEQ ID NO: 11) |
| rIL-α-Forward: | 5'-CTACCGCTTTCCCCACTTCAG-3' | (SEQ ID NO: 12) |
| rIL-α-Reverse: | 5'-TCCTCAGCTCCTTGATGGTCT-3' | (SEQ ID NO: 13) |

Example 5. SDP and SDP-4 Inhibit Hydrogen Peroxide-Mediated Redox Signaling

Electron Paramagnetic Resonance (EPR) spectroscopy was used to selectively quantify concentrations of hydrogen peroxide ($H_2O_2$) in solution. Specifically, 20 μM of $H_2O_2$ was added to aqueous solutions containing 0, 0.5, 1.0, or 5.0% of PASF, SDP, or SDP-4, and was incubated at room temperature for 24 hours. To quantitate remaining $H_2O_2$ levels following incubation, 200 μM of the $H_2O_2$-specific spin probe 1-hydroxy-3-methoxycarbonyl-2,2,5,5-tetramethylpyrrolidine (CMH) was then added along with assay reagents 4-acetamidophenol (AAP, 1 mM), diethylenetri-aminepentaacetic acid (DTPA, 200 μM), and horseradish peroxidase (HRP, 1 U/mL). This mixture was then incubated at 37° C. for 30 minutes, during which time AAP is oxidized by $H_2O_2$ in the presence of HRP to generate phenoxyl radicals, which then react with the CMH spin probe to generate a CM radical, which is detected and quantified by EPR.

Results:

PASF elevated EPR signal amplitude above control levels with increasing protein concentration, indicating that PASF oxidizes the $H_2O_2$ spin probe directly. In contrast, addition of SDP evoked a concentration-dependent reduction in EPR signal amplitude, demonstrating that SDP proteins scavenge $H_2O_2$ by 40% at 5.0% SDP. These reductions were even more robust in the presence of SDP-4 proteins, whereby 5.0% SDP-4 reduced $H_2O_2$ levels by over 80%. See FIG. 5.

The capacity of SDP and more so SDP-4 to scavenge $H_2O_2$ and inhibit redox signaling is tyrosine-driven. Tyrosine is a known long-term acting antioxidant due to its aromatic and hydroxyl-containing functional group which permit ease of electron shuffling inherent to redox signaling (see Van Overveld et al., *Chemico-Biological Interactions*, 127(2000), 151-161). SDP and SDP-4 possess high tyrosine composition (greater than or equal to about 13% wt./wt.), and these proteins enhance tyrosine delivery to the ocular surface. The physiologic solubility of tyrosine is 0.4 mg/mL, yet tyrosine solubility in 1% wt./vol. SDP over three times greater (1.3 mg/mL), thus providing a proportional increase per 1% wt./vol. of SDP. Furthermore, the aqueous solubility of SDP and SDP-4 exceeds 80% wt./vol., far greater than other known proteins.

Example 6. Fractionation and Molecular Weight Distribution of SDP Protein Solutions Fractionation of a regenerated SDP solution was accomplished through a series of centrifugation steps utilizing Amicon Ultra 15 mL centrifugal filters of 100, 50, 30, and 10 kDa MW cutoffs (EMD-Millipore, MA, USA). To evaluate the molecular weight range of the fractionated SDP solutions, the electrophoretic mobility of the SDP protein was visualized using SDS-PAGE and compared to that of unfractionated SDP solution. SDS-PAGE of the unfractionated SDP indicated a wide molecular weight distribution of SDP protein within the solution, as evidenced by a large smear located approximately between the 300 kDa and 30 kDa molecular mass ranges.

Fractionation of the regenerated SDP solution produced four fractions ranging from high to low molecular weight SDP proteins (SDP-1, SDP-2, SDP-3, and SDP-4, respectively). See FIG. 6. When compared to unfractionated SDP solution, SDS-PAGE of the high molecular weight solution produced a smear indicating an approximate molecular weight distribution between the 300 kDa and 100 kDa range (SDP-1 and SDP-2), while the low molecular weight solution produced a smear indicating a molecular weight distribution predominantly in the 30 kDa range (SDP-3 and SDP-4), and thus confirming the fractionation of SDP into high and low molecular weight SDP protein solutions.

For example, a 50 mg/mL aqueous SDP solution derived from *Bombyx mori* silkworm cocoons was used for the following study. Fractionation of SDP protein fragments was accomplished using Amicon Ultra 15 mL centrifugal filters of 100, 50, 30, and 10 kDa MW cutoffs (EMD-Millipore, MA, USA). Briefly, 15 mL of a 40 mg/mL SDP stock solution was added to a centrifugal filter with 100 kDa MW cutoff and spun down at 4,000×g for 30 minutes for isolation of SDP protein fragments of 100 kDa MW and above. The isolated concentrate was collected and the filtrate was subsequently transferred to a centrifugal filter with 50 kDa MW cutoff and spun down again at 4,000×g for 30 minutes to isolate SDP protein fragments of ~50 kDa MW. The isolated concentrate was collected and the filtrate was then transferred to a centrifugal filter with 30 kDa MW cutoff and spun down again at 4,000×g for 30 minutes to isolate SDP protein fragments of ~30 kDa MW. The isolated concentrate was collected and the filtrate was then transferred to a centrifugal filter with 10 kDa MW cutoff and spun down again at 4,000×g for 30 minutes to isolate SDP protein fragments of ~10 kDa MW. The collected concentrates from each MW cutoff were individually washed, 6 times, with 5 mL of $dH_2O$ and spun down again at 4,000×g for 30 minutes using centrifugal filters with the respective MW cutoff filter size for each concentrate. Fractionation of SDP protein fragments was verified using SDS-PAGE (FIG. 6) and Coomassie blue R-250 staining (Gibco, Invitrogen Corporation, Grand Island, N.Y.).

ImageJ analysis of the SDP-4 fraction showed that SDP-4 has an average molecular weight of 34 kDa, as determined by SDS-PAGE. Similar filtration of PASF (30 kDa MWCO filter) provided a lower molecular weight fraction having an average molecular weight of 51 kDa, and a separate higher average molecular weight fraction (90 kDa). Further analysis of SDP fractions and PASF fractions is summarized in the table below.

|  |  | SDP-4 | SDP-1-3 | SDP | PASF-4 | PASF-1-3 | PASF |
|---|---|---|---|---|---|---|---|
| kDa Range | 100-10 | 85.3% | 76.2% | 77.3% | 81.1% | 52.8% | 50.2% |
|  | 85-10 | 83.6% | 71.5% | 73.0% | 77.4% | 48.4% | 45.2% |
|  | 85-15 | 72.1% | 66.7% | 66.2% | 71.3% | 44.8% | 41.6% |
|  | 60-20 | 57.7% | 49.1% | 48.5% | 53.4% | 31.6% | 27.1% |
|  | 50-25 | 39.0% | 31.4% | 30.8% | 34.6% | 20.1% | 15.7% |
| Average MW (kDa) |  | 34 | 57 | 53 | 51 | 90 | 97 |

Fractions having average molecular weights of less than 10 kDa are unstable in solution and form gels within 1-2 hours and are therefore typically removed from the SDP compositions and fractions.

Example 7. SDP Stability Study of SDP-4 and SDP-1-3

The stability study described in Example 3 was also performed on SDP-4 and a low average molecular weight fraction of isolated native fibroin (PASF-4). Sonication-induced secondary structure formation and gelation was found to be absent in the SDP-4 solution after sonication challenge. The SDP-4 solution remained clear and free flowing. The lack of gelation indicates the significantly greater protein stability of SDP-4, whereas the PASF-4 solution gelled within 2 hours after sonication challenge, indicating its instability in solution. SDP-4 remained in solution throughout the time course of the experiment (96 hours).

The stability study was also carried out on higher molecular weight fractions of SDP (equivalent to the combination of SDP-1, SDP-2, and SDP-3; referred to as SDP-1-3). The aqueous solution of SDP-1-3 remained a free-flowing solution throughout the time course of the experiment (more than 24 hours). However, the higher molecular weight fractions of isolated native fibroin (PASF-1-3) gelled within 15 minutes, indicating secondary protein structure formation and hence instability.

Experimental conditions: 1 mL of 4% wt./wt. solutions of SDP-4, SDP-1-3, PASF-4, and PASF-1-3 were subjected to sonication at 60% amplitude, 20 Hz pulse frequency, for 3 minutes. Solutions were then monitored at room temperature until gelation had occurred for PASF-4 and PASF-1-3. SDP-4 and SDP-1-3 remained in solution for more than 96 hours and 24 hours, respectively (the time course of this study).

Example 8. Enhanced Wound Healing Properties of SDP-1 and SDP-2

Wound healing was evaluated on confluent hCLE monolayers subjected to a scratch assay in the absence or presence of SDP fractions (10 mg/mL). Wound closure rates were evaluated using time-lapse microscopy. Proliferation of hCLEs treated with SDP or PBS controls were evaluated by MTT assay.

Figure 7:
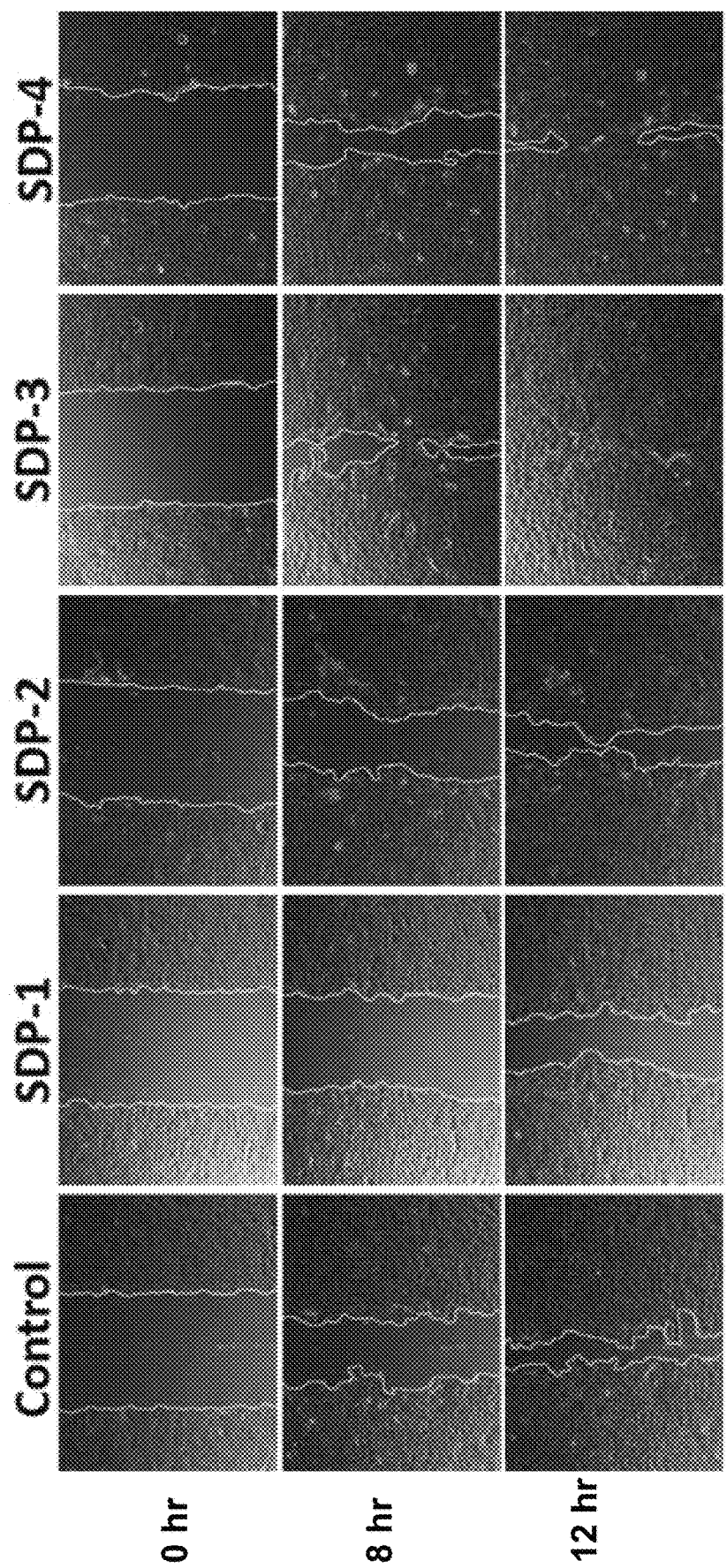
FIG. 7. Representative images from in vitro wound healing assays demonstrate that cell growth and migration into the cell-free region (wound), outlined in white, is significantly accelerated in the presence of 5-mg/mL SDP-3 or SDP-4.
Figure 8:
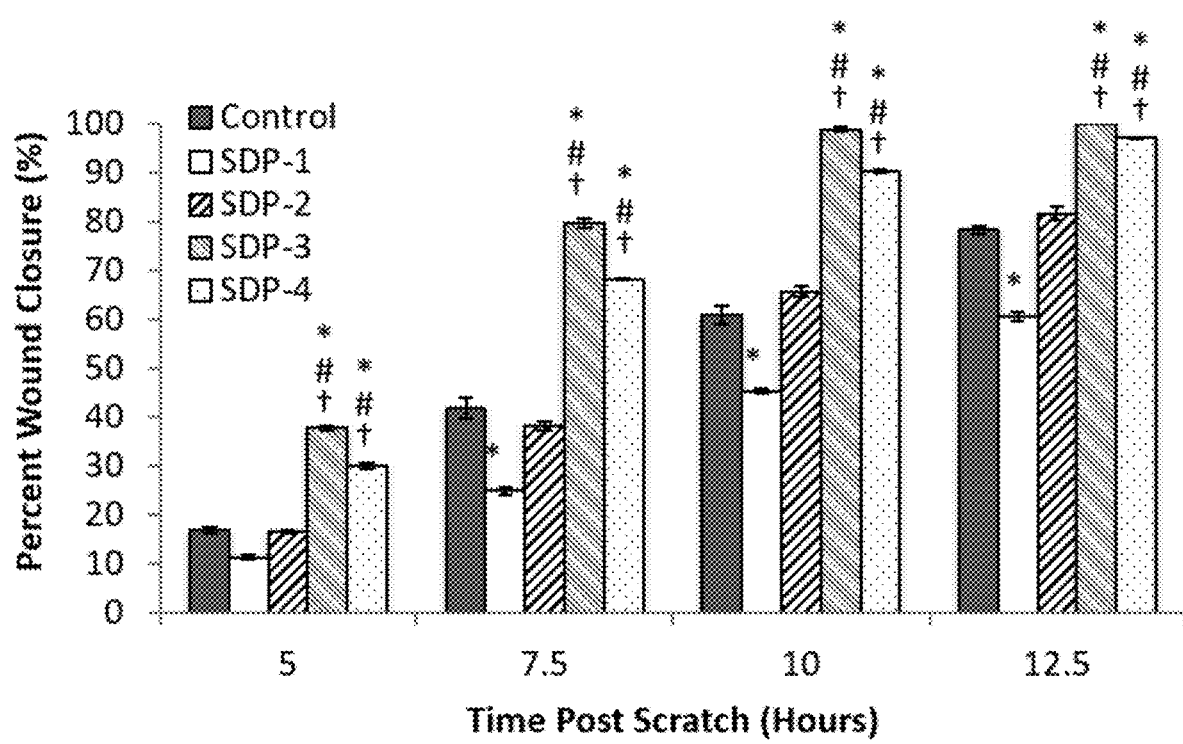
FIG. 8. Summary bar graph illustrating percent wound closure at indicated time points during the scratch wound assay (*$p<0.05$ vs Control), (#$p<0.05$ vs SDP-1, n=3), (†$p<0.05$ vs SDP-2, n=3).
Figure 9:
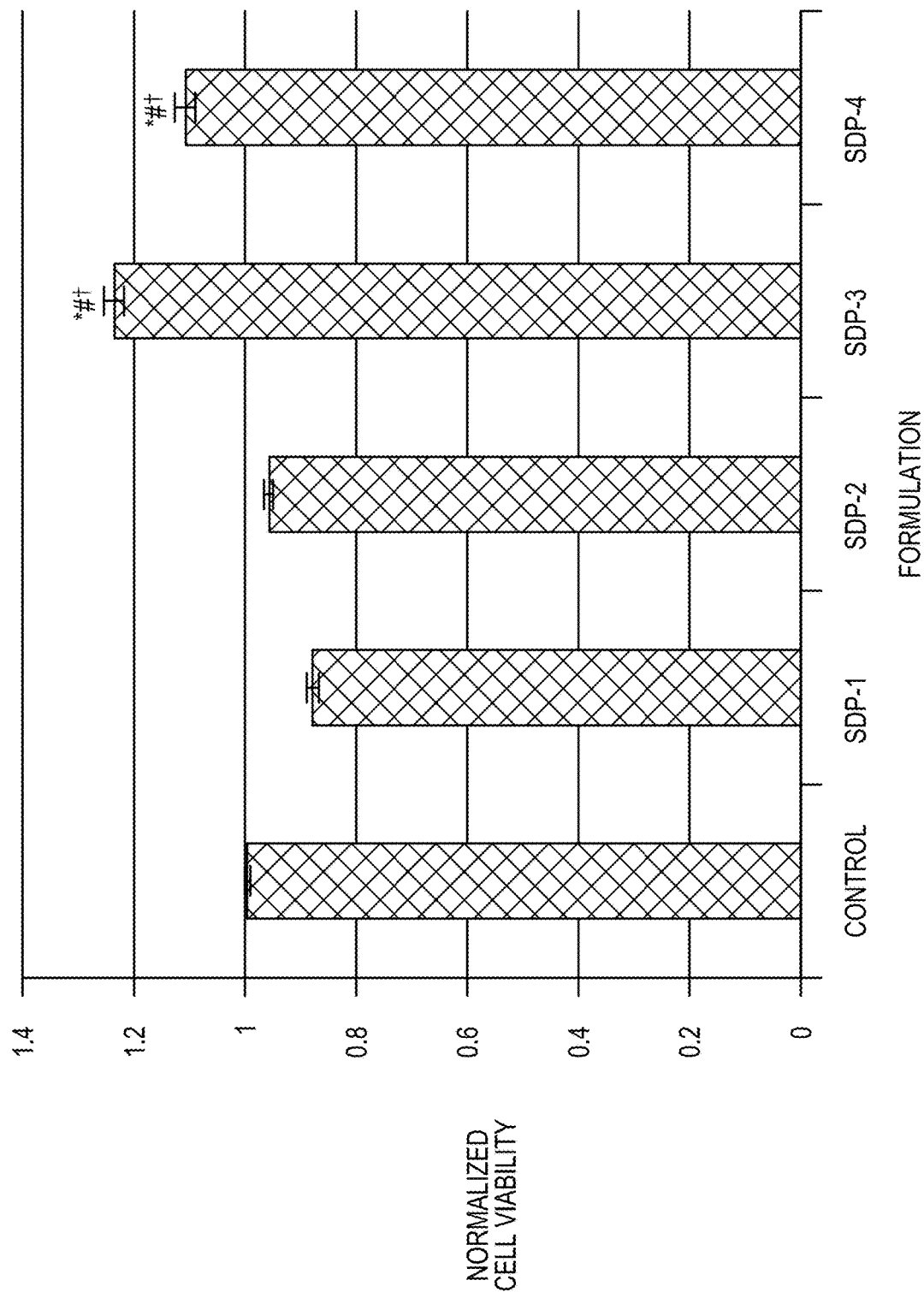
FIG. 9. MTT analysis of epithelial cell viability in hCLE cultures treated with 5-mg/mL of fractionated SDPs or (saline buffer) control. Treatment with SDP-3 and SDP-4 significant increased cell proliferation relative to control cells. Treatment with SDP-1 or SDP-2 did not change cell proliferation relative to controls (*p<0.05 vs. Control, n=3; #p<0.05 vs. SDP-1, n=3; † p<0.05 vs. SDP-2, n=3).

SDP MW had a critical impact on the behavior of injured hCLE cultures. Low average M.W. fractions of <100 kDa (i.e., SDP-3 and SDP-4) significantly accelerated repopulation of denuded (scratched) hCLE cells vs. PBS treated control cultures by 6 hours, which persisted until confluency (16 hours vs. 20 hours for controls) (FIGS. 7 and 8). SDP-3 and SDP-4 significantly increased hCLE proliferation vs. control cultures treated with PBS, as evidenced by increased (>50%) metabolic activity by the MTT assay results. Conversely, high MW fractions of >100 kDa (i.e., SDP-1 and SDP-2) inhibited repopulation, although pro-proliferative effects of SDP were still observed (FIG. 9). These results demonstrate the enhanced potency effect that SDP-3 and SDP-4 fractions have on hCLE cell migration outcomes in vitro.

Example 9. Anti-Inflammatory Properties

Inflammatory properties of SDP fractions 1-4 were evaluated on hCLE cultures stimulated with the pro-inflammatory cytokine tumor necrosis factor-alpha (TNF-α, 1 ng/mL) in the presence or absence of SDP fractions. qPCR was used to quantitate subsequent expression of inflammatory genes. Secretion of these proteins by hCLE cells was evaluated by ELISA. Functional significance of altered inflammatory gene expression was assessed using a Transwell co-culture assay with TNF-α stimulated hCLE cultures and a promyelocytic immune cell line (HL-60), performed in the presence or absence of SDP fractions.

Figure 10:
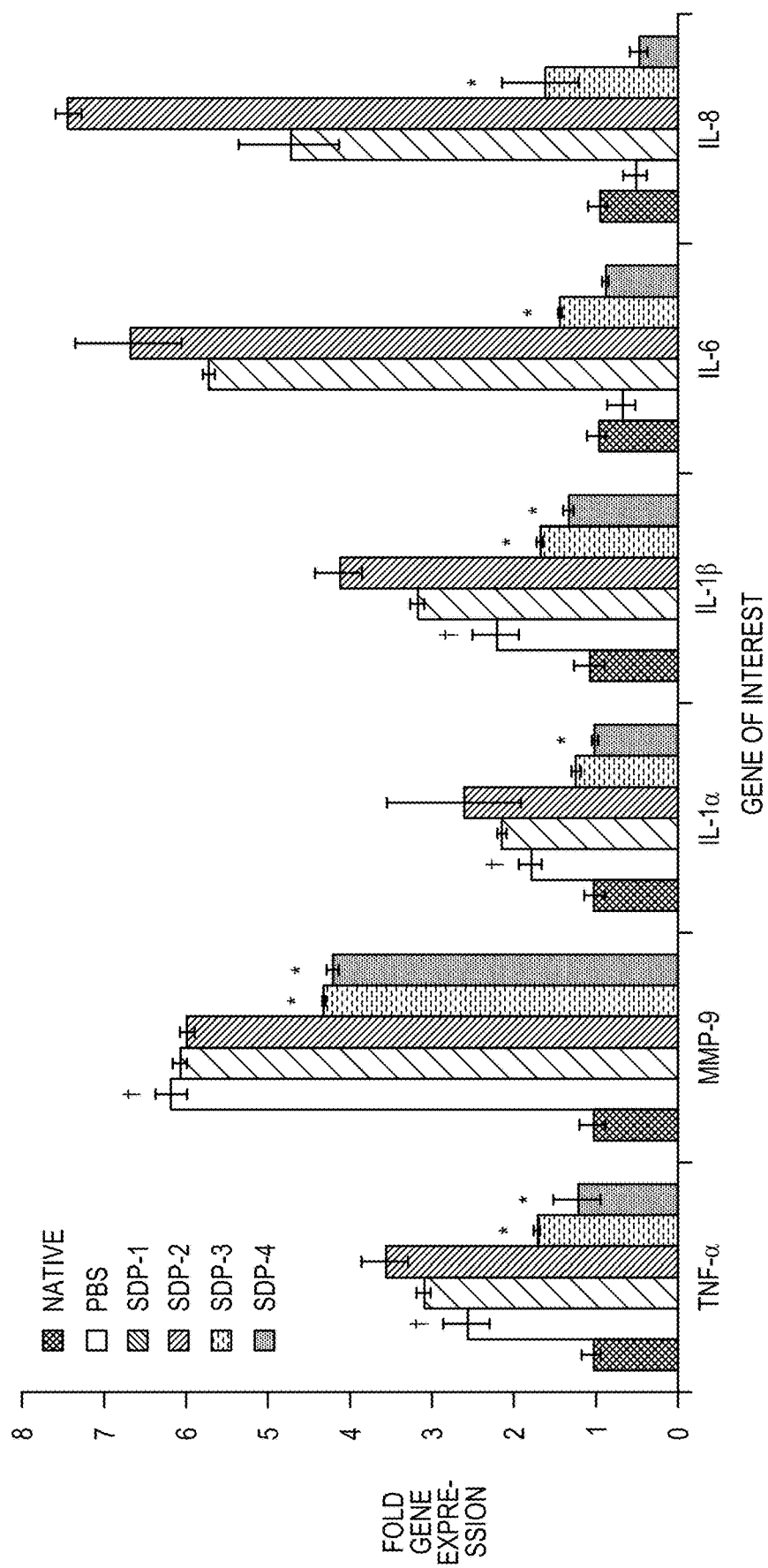
FIG. 10. qPCR summary of TNF-α, MMP-9, and Inter-leukins-1α/β, -6, and -8 transcription in hCLE cells untreated (native) or stimulated with TNF-α to initiate inflammatory signaling, and treated with 1 mg/mL of fractionated SDP. Treatment with SDP-3 and SDP-4 significantly decreased transcription of the defined inflammatory genes, relative to control cells treated with PBS. († p<0.05 vs Native, n=3; *p<0.05 vs Control, n=3).
Figure 11:
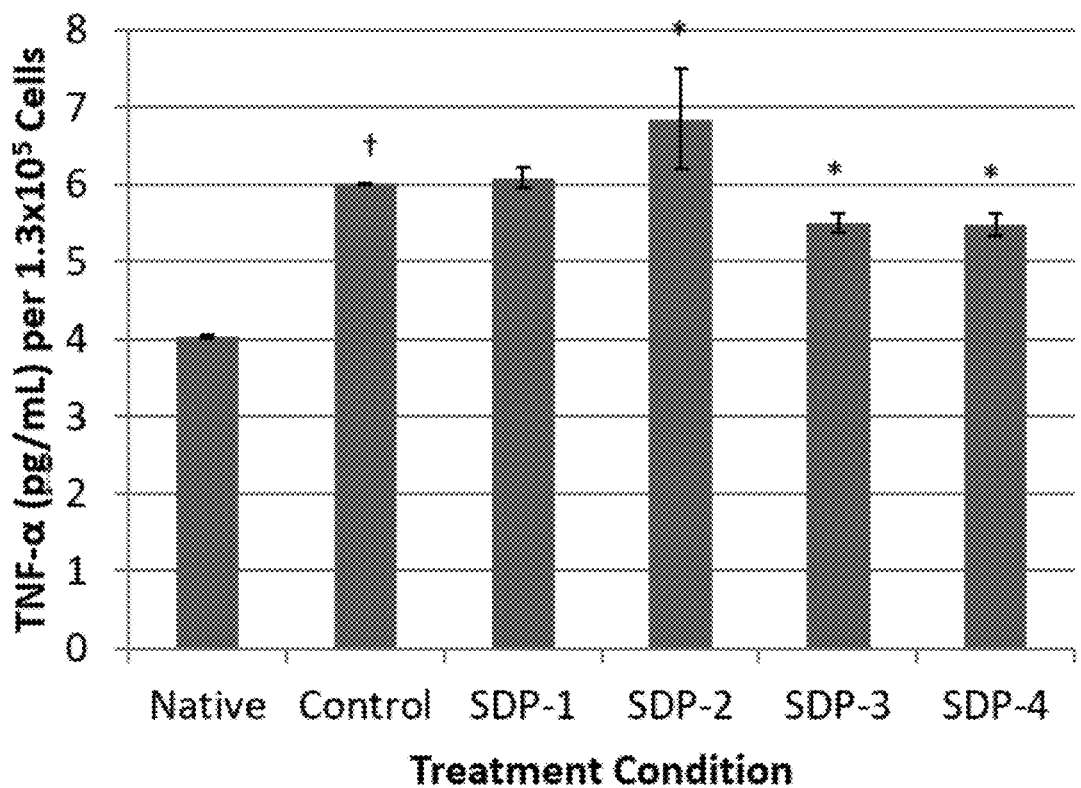
FIG. 11. ELISA analysis of TNF-α cytokine secretion by hCLE cells untreated (native) or stimulated with TNF-α to initiate inflammatory signaling, and treated with 1 mg/mL of SDP fractions. Treatment with SDP-3 and SDP-4 significantly decreased secretion of the pro-inflammatory cytokine TNF-α, while SDP-2 significantly increased secretion, relative to control cells treated with PBS. († p<0.05 vs Native, n=3), (*p<0.05 vs Control, n=3).
Figure 12:
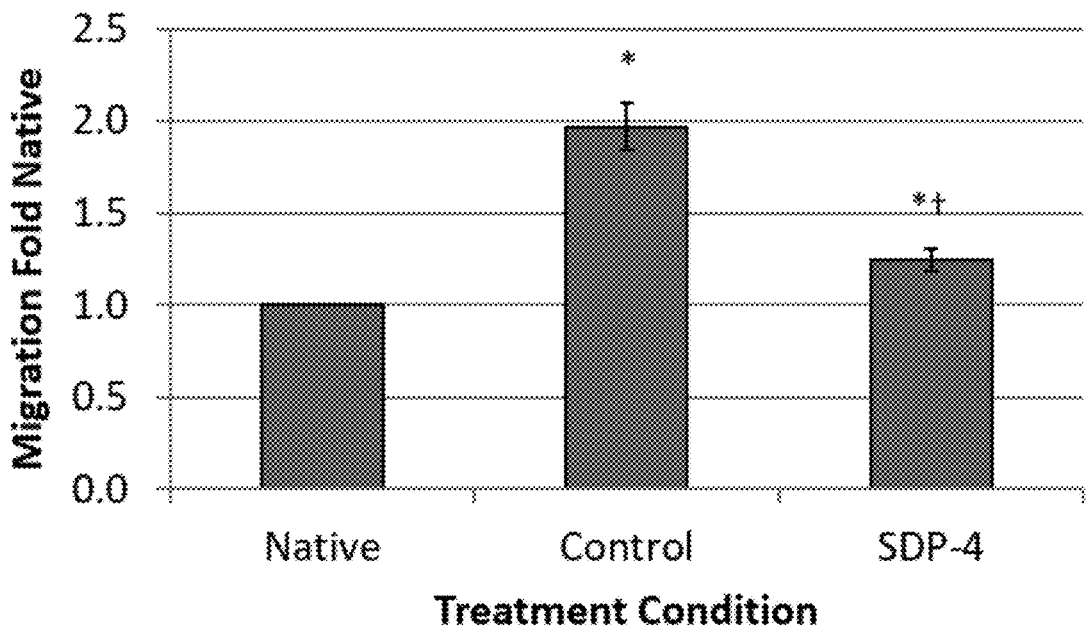
FIG. 12. Summary of Transwell migration assay demonstrating that treatment with TNF-α significantly increased HL-60 inflammatory cell migration relative to untreated (native) cultures. Addition of SDP-4 (1 mg/mL) resulted in a significant reduction of TNF-α driven HL-60 cell migration († p<0.05 vs Control, n=3; *p<0.05 vs Native, n=3).

TNF-α challenged hCLE cultures robustly increased expression of inflammatory genes TNF-α, interleukins 6 and 1 α/β, and protease MMP-9, which expression was significantly attenuated with low MW SDP (FIG. 10). This translated into significant reductions in the secretion of TNF-α and MMP-9 by stimulated hCLEs as measured by ELISA at 8 hours (FIG. 11). TNF-α-challenged hCLEs evoked significant recruitment of HL-60 cells that was normalized by the addition of SDP-4, demonstrating a functional relationship between impaired inflammatory signaling and downstream immune responses in vitro (FIG. 12).

Example 10. Preparation of OTC and Anti-Inflammatory Eye Drop Formulations

An eye drop composition can be prepared to take advantage of the therapeutic properties of SDP to treat the ocular system because of disease or injury. SDP molecules can be optionally isolated based on molecular weights (e.g., SDP-1, SDP-2, SDP-3, SDP-4, or a combination thereof), or used as a whole composition (e.g., SDP). A composition of protein molecules of low average molecular weight, such as less than about 40 kDa, can be prepared and is referred to as SDP-4. A second composition of protein molecules that includes all molecular weights of the SDP composition or molecules more than about 40 kDa can also be prepared. Each composition can include water, at least one buffer or buffer system (e.g., phosphate buffered saline (PBS), citrate, borate, Tris, 4-(2-hydroxyethyl)-1-piperazineethanesulfonic acid (HEPES)), optionally at least one preservative (e.g., perborate, benzalkonium chloride (BAK)) and optionally at least one additional excipient, surfactants, stabilizers or salt (e.g., sulfanilic acid, trehalose, glycerin, ethylenediaminetetraacetic acid (EDTA), polyethylene glycol (PEG), mannitol, polysorbate, sodium chloride (NaCl), magnesium chloride ($MgCl_2$), calcium chloride ($CaCl_2$), or lithium bromide (LiBr)).

The eye formulation containing the first compositions above can be applied as a therapeutic product to a dry eye disease patient, a wounded patient, or a surgical wound of an otherwise healthy patient (e.g., for post-refractive or cataract surgery). The disease or injury can be monitored over time for inflammation and wound closure rate, and for patient comfort and pain assessment. The second compositions can be used in over-the-counter products, such as an artificial tears eye drop product, as a protein excipient to help with enhancing formulation wetting, spreading, and patient comfort.

An example of an eye drop formulation would contain as low as 0.1% wt./vol. SDP-4 or SDP to as high as 10% wt./vol. SDP-4 or SDP. The SDP-4 or SDP material would be dissolved into purified water, where a buffer system such as citric acid buffer, Tris buffer, PBS buffer, or borate buffer would be created in a 1 mmol to 1,000 mmol concentration. Additional excipient ingredients may be added to the formulation. A surfactant, such as polysorbate, could be added in the range of a 0.01%-0.1% wt./vol. concentration. Stabilizing sugar molecules can be added, such as trehalose, dextrose, or sucrose, at concentrations ranging from 10 mmol-500 mmol. Demulcent molecules can be added as ocular lubricants, such as PEG, carboxy methyl cellulose, hypromellose, hydroxypropyl methylcellulose, or glycerin, at concentrations ranging from 0.1%-2.0% wt./vol. Salts may also be added to reduce molecular interactions and stabilize the formulation, such as NaCl, $MgCl_2$, $CaCl_2$, or LiBr, at concentration ranging from 10 mmol-500 mmol. Amino acid molecules can be added as stabilizing agents, such as L-glutamine or L-arginine, at concentrations ranging from 10 mmol-500 mmol. Chelating agents can be added as stabilizing agents, such as EDTA, at concentrations ranging from 0.01%-0.1% wt./vol. Anti-microbial agents can be added to the formulation, such as perborate or BAK, at concentrations of up to 0.015% wt./vol.

Below is a table of a few example base formulations that have been produced containing the SDP-4 and/or SDP molecules, in which additional additives or excipients can be added to enhance formulation applications described above:

SDP, or an SDP fraction such as SDP-4, can also be added to known eye formulations such as commercial and prescription eye drops and ointments to improve wetting and patient comfort. Examples of ophthalmic solutions that SDP or SDP-4 can be added to include brimonidine tartrate, brimonidine tartrate/timolol maleate, alcaftadine, bimatoprost, cyclosporine, gatifloxacin, ketorolac tromethamine, or lifitegrast ophthalmic solutions. Examples of other formulations that SDP or SDP-4 can be added to are described in U.S. Pat. Nos. 5,468,743; 5,880,283; 6,333,045; 6,562,873; 6,627,210; 6,641,834; 6,673,337; 7,030,149; 7,320,976; 7,323,463; 7,351,404; 7,388,029; 7,642,258; 7,842,714; 7,851,504; 8,008,338; 8,038,988; 8,101,161; 8,133,890; 8,207,215; 8,263,054; 8,278,353; 8,299,118; 8,309,605; 8,338,479; 8,354,409; 8,377,982; 8,512,717; 8,524,777; 8,541,463; 8,541,466; 8,569,367; 8,569,370; 8,569,730; 8,586,630; 8,629,111; 8,632,760; 8,633,162; 8,642,556; 8,648,048; 8,648,107; 8,664,215; 8,685,930; 8,748,425; 8,772,338; 8,858,961; 8,906,962; and 9,248,191, and 7,314,938; 7,745,460; 7,790,743; 7,928,122; 8,084,047; 8,168,655; 8,367,701; 8,592,450; 8,927,574; 9,045,457; 9,085,553; 9,216,174; 9,353,088; and 9,447,077.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

In accordance with 35 U.S.C. 102(b)(2)(c), (1) the subject matter disclosed was developed and the claimed invention was made by, or on behalf of, the parties to a joint research agreement that was in effect on or before the effective filing date of the claimed invention; (2) the claimed invention was made as a result of activities undertaken within the scope of the joint research agreement; and (3) the names of the parties to the joint research agreement are (a) Silk Technologies, Ltd. and (b) Cornell University. The inventors have assigned their rights in the invention to Silk Technologies, Ltd. or Cornell University.

|  | Composition | | | | |
| --- | --- | --- | --- | --- | --- |
| Ingredient | 1 | 2 | 3 | 4 | 5 |
| SDP-4 or SDP | 5 or 10 g | 5 or 10 g | 5 or 10 g | 5 or 10 g | 5 or 10 g |
| Phosphate | 10 mmol | — | — | — | — |
| NaCl | 137 mmol | — | — | — | — |
| KCl | 2. 7 mmol | — | — | — | — |
| Citric Acid | — | 82 mmol | 8 mmol | — | — |
| Trisodium Citrate | — | 18 mmol | 92 mmol | — | — |
| Tris Hydrochloric Acid | — | — | — | 7.02 g | 0.76 g |
| Tris Base | — | — | — | 0.67 g | 5.47 g |
| Water | 1 L | 1 L | 1 L | 1 L | 1 L |
| pH | 7.4 | 3.0 | 6.2 | 7.2 | 9.0 |

What is claimed is:

1. A fibroin-derived protein composition that possesses enhanced stability in an aqueous solution compared to native silk fibroin consisting of the a fibroin-derived protein composition wherein:
   the primary amino acid sequences of the fibroin-derived protein composition differ from native fibroin by at least 4% with respect to the absolute values of the combined differences in amino acid content of serine, glycine, and alanine;
   cysteine disulfide bonds between the fibroin heavy and fibroin light protein chains of fibroin are reduced or eliminated;
   the composition has a serine content that is reduced by greater than 25% compared to native fibroin protein, wherein the serine content is at least about 5%; and
   wherein the average molecular weight of the fibroin-derived protein composition is less than 40 kDa and greater than 10 kDa, and 39%+/−10% of the protein chains of the protein composition have a molecular weight within the range of 25 kDa to 50 kDa.

2. The protein composition of claim 1 wherein the protein composition does not gel upon sonication of an aqueous solution of the protein composition at concentrations of up to 10% w/w.

3. The protein composition of claim 1 wherein the protein composition comprises less than 8% serine amino acid residues.

4. The protein composition of claim 1 wherein the protein composition comprises greater than 46.5% glycine amino acids.

5. The protein composition of claim 1 wherein the protein composition comprises greater than 30.5% alanine amino acids.

6. The protein composition of claim 1 wherein the protein composition completely re-dissolves in water after being dried to a thin film.

7. The protein composition of claim 1 wherein the protein composition lacks beta-sheet protein structure in aqueous solution.

8. The protein composition of claim 1 wherein the protein composition maintains an optical absorbance in aqueous solution of less than 0.25 at 550 nm after at least five seconds of sonication.

9. An ophthalmic formulation comprising the protein composition of claim 1 and water, and optionally one or more of a buffering medium, a salt, a stabilizer, a preservative, and a lubricant.

10. A method for reducing inflammation comprising administering the fibroin-derived protein composition according to claim 1 to inflamed tissue
    thereby reducing transcription factor signaling within cell nuclei of the tissue, thereby reducing the inflammation.

11. The method of claim 10 wherein the administration to inflamed tissue reduces transcription of one or more of the inflammatory genes TNF-α, MMP-9, IL-1β, and IL-6.

12. The method of claim 10 wherein the administration is to the cornea and the administration reduces the presence of MMP-9 in the cornea.

13. The method of claim 10 wherein the administration is to the eye and the administration reduces inflammation on the ocular surface.

14. The method of claim 10 wherein the reduction in inflammation is accompanied by increased cell migration rates at the point of inflammation.

15. The method of claim 10 wherein the protein composition has an average molecular weight less than 35 kDa.

16. The method of claim 10 wherein the fibroin-derived protein composition is dissolved in an ophthalmic formulation comprising one or more of a buffering medium, a salt, a stabilizer, a preservative, and a lubricant.

17. The method of claim 10 wherein the inflammation is caused by an ocular condition, wherein the ocular condition is dry eye syndrome, corneal ulcer, corneal erosion, corneal abrasion, corneal degeneration, corneal perforation, corneal scarring, epithelial defect, keratoconjunctivitis, idiopathic uveitis, corneal transplantation, age-related macular degeneration, diabetic eye, blepharitis, glaucoma, ocular hypertension, post-operative eye pain and inflammation, posterior segment neovascularization, proliferative vitreoretinopathy, cytomegalovirus retinitis, endophthalmitis, choroidal neovascular membrane, vascular occlusive disease, allergic eye disease, tumor, retinitis pigmentosa, eye infection, scleritis, ptosis, miosis, eye pain, mydriasis, neuralgia, cicatrizing ocular surface disease, ocular infection, inflammatory ocular disease, ocular surface disease, corneal disease, retinal disease, ocular manifestations of systemic diseases, hereditary eye condition, ocular tumor, increased intraocular pressure, herpetic infection, ptyrigium or scleral tumor, wound sustained to ocular surface, post-photorefractive keratotomy eye pain and inflammation, thermal or chemical burn to the cornea, scleral wound, or keratoconus and conjunctival wound.

18. The method of claim 17 wherein the inflammation is caused by dry eye syndrome.

* * * * *

UNITED STATES PATENT AND TRADEMARK OFFICE
CERTIFICATE OF CORRECTION

PATENT NO. : 11,242,367 B2
APPLICATION NO. : 16/324844
DATED : February 8, 2022
INVENTOR(S) : Lawrence et al.

Page 1 of 1

It is certified that error appears in the above-identified patent and that said Letters Patent is hereby corrected as shown below:

In the Claims

• In Claim 1, at Column 43, Line 19, after "consisting of the" please delete "a".

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*